United States Patent
Lee et al.

(10) Patent No.: US 9,763,639 B2
(45) Date of Patent: Sep. 19, 2017

(54) TOMOGRAPHY IMAGING APPARATUS AND METHOD OF RECONSTRUCTING TOMOGRAPHY IMAGE

(71) Applicant: SAMSUNG ELECTRONICS CO., LTD., Suwon-si (KR)

(72) Inventors: Kyoung-yong Lee, Hwaseong-si (KR); Duhgoon Lee, Yongin-si (KR); Baeg-gi Min, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 206 days.

(21) Appl. No.: 14/838,522

(22) Filed: Aug. 28, 2015

(65) Prior Publication Data
US 2016/0256127 A1    Sep. 8, 2016

(30) Foreign Application Priority Data
Mar. 5, 2015   (KR) .......................... 10-2015-0031114

(51) Int. Cl.
*G06K 9/00* (2006.01)
*A61B 6/00* (2006.01)
(Continued)

(52) U.S. Cl.
CPC ............ *A61B 6/5288* (2013.01); *A61B 6/032* (2013.01); *A61B 6/486* (2013.01); *A61B 6/5264* (2013.01);
(Continued)

(58) Field of Classification Search
CPC ....... A61B 6/5288; A61B 6/032; A61B 6/486; A61B 6/5264; G06T 7/0012; G06T 11/003; G06T 2207/10081
See application file for complete search history.

(56) References Cited

U.S. PATENT DOCUMENTS

| 5,744,802 A * | 4/1998 | Muehllehner | G01T 1/1648 250/363.03 |
| 6,242,743 B1 * | 6/2001 | DeVito | A61B 6/037 250/363.01 |

(Continued)

FOREIGN PATENT DOCUMENTS

| WO | 2011/097927 A1 | 8/2011 |
| WO | 2014/005178 A1 | 1/2014 |

OTHER PUBLICATIONS

J-H Kim et al., "A rigid motion correction method for helical computed tomography (CT)", Phys Med Biol, 2015, 29 pgs. total.
(Continued)

*Primary Examiner* — Shefali Goradia
(74) *Attorney, Agent, or Firm* — Sughrue Mion, PLLC

(57) ABSTRACT

A tomography imaging apparatus is provided, including: a data acquisition unit configured to acquire a plurality of partial data respectively corresponding to a plurality of consecutive angular sections by performing a tomography scan on a moving object; and an image processing unit configured to measure global motion of the object and motion of a first region in the object based on the plurality of partial data, acquire first information representing motion of the object by reflecting the global motion in the motion of the first region, and reconstruct a final tomography image representing the object based on the first information.

28 Claims, 26 Drawing Sheets

(51) Int. Cl.
    *A61B 6/03*        (2006.01)
    *G06T 7/00*        (2017.01)
    *G06T 11/00*     (2006.01)

(52) U.S. Cl.
    CPC .......... *G06T 7/0012* (2013.01); *G06T 11/003* (2013.01); *G06T 2207/10081* (2013.01)

(56) References Cited

U.S. PATENT DOCUMENTS

| | | |
|---|---|---|
| 7,678,063 B2 | 3/2010 | Felmlee et al. |
| 8,184,883 B2 | 5/2012 | Grass et al. |
| 8,401,267 B2 * | 3/2013 | Nakai ................... A61B 6/032 382/132 |
| 8,411,915 B2 | 4/2013 | Wischmann et al. |
| 8,731,268 B2 | 5/2014 | Li et al. |
| 2002/0025017 A1 | 2/2002 | Stergiopoulos et al. |
| 2008/0298539 A1 * | 12/2008 | Nakanishi .............. A61B 6/032 378/15 |
| 2011/0142315 A1 | 6/2011 | Hsieh et al. |
| 2011/0142316 A1 * | 6/2011 | Wang .................... G06T 11/006 382/131 |
| 2011/0228897 A1 | 9/2011 | Kobayashi |
| 2012/0305780 A1 | 12/2012 | Thiruvenkadam et al. |
| 2013/0114871 A1 | 5/2013 | Berkus et al. |
| 2015/0243045 A1 * | 8/2015 | Ra ........................ G06T 7/0024 382/131 |

OTHER PUBLICATIONS

International Search Report for PCT/KR2015/013536 dated Mar. 21, 2016 [PCT/ISA/210].
Written Opinion for PCT/KR2015/013536 dated Mar. 21, 2016 [PCT/ISA/237].

\* cited by examiner

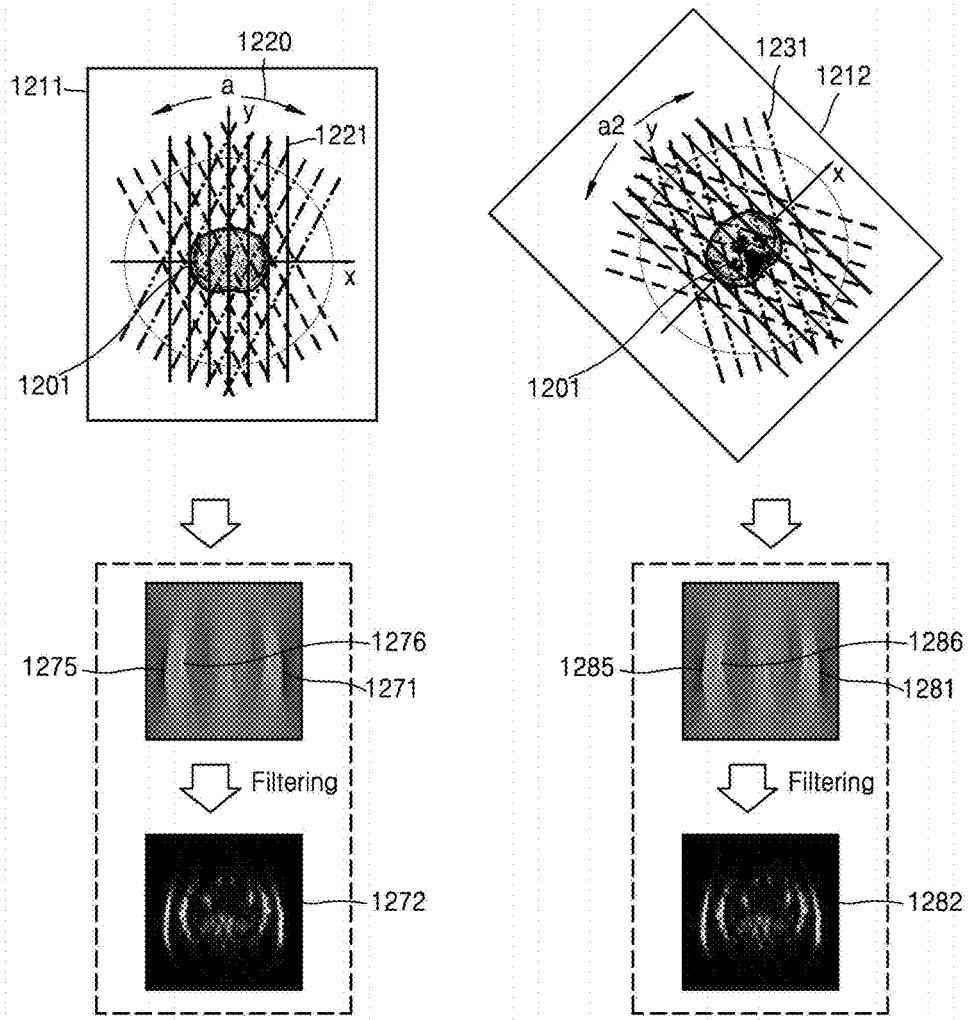

● : Control point

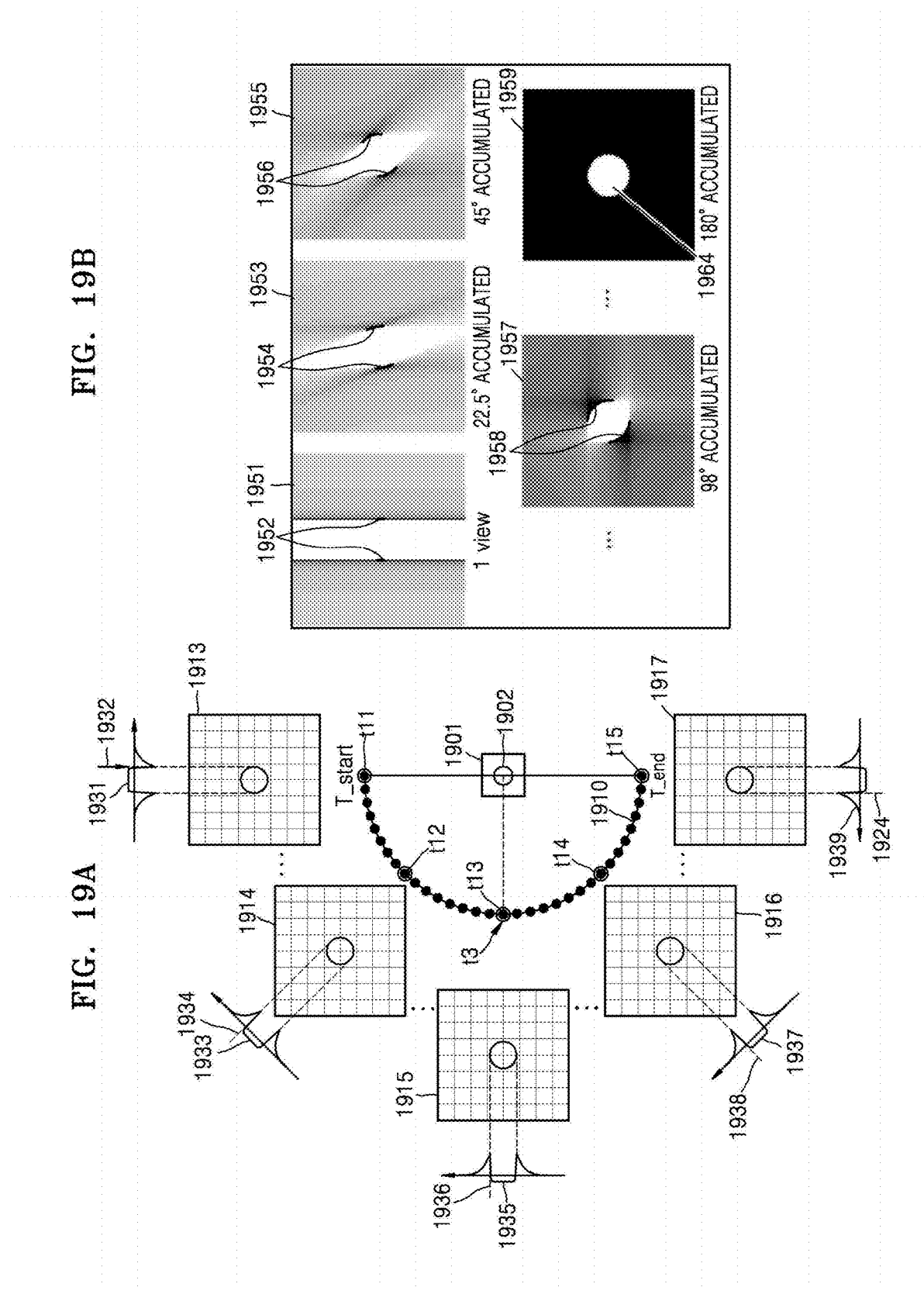

TOMOGRAPHY IMAGING APPARATUS AND METHOD OF RECONSTRUCTING TOMOGRAPHY IMAGE

CROSS-REFERENCE TO RELATED APPLICATION

This application claims the benefit of Korean Patent Application No. 10-2015-0031114, filed on Mar. 5, 2015, in the Korean Intellectual Property Office, the disclosure of which is incorporated herein in its entirety by reference.

BACKGROUND

1. Field

One or more exemplary embodiments relate to a tomography imaging apparatus and a method of reconstructing a tomography image, and more particularly, to a tomography imaging apparatus for reconstructing a tomography image by performing a tomography scan on a moving object and a method of reconstructing a tomography image therefor.

2. Description of the Related Art

Medical imaging apparatuses are used to acquire images showing an internal structure of an object. The medical imaging apparatuses are non-invasive examination apparatuses that capture and process images of details of structures, tissue, fluid flow, etc., inside a body and provide the images to a user. A user, e.g., a medical practitioner, may use medical images output from the medical imaging apparatuses to diagnose a patient's condition and diseases.

A tomography apparatus is a representative example of an apparatus for photographing an object by emitting X-rays toward a patient. In detail, a computed tomography (CT) apparatus may be an example of a tomography imaging apparatus.

Among medical image processing apparatuses, a CT apparatus is capable of providing a cross-sectional image of an object. Furthermore, the CT apparatus may represent an internal structure (e.g., organs such as a kidney, a lung, etc.) of the object without superimposing images, as compared to a general X-ray apparatus. Due to these advantages, a CT apparatus has been widely used for precise diagnosis of diseases. A medical image acquired by a tomography imaging apparatus is hereinafter referred to as a tomography image. In detail, a medical image acquired by a CT apparatus is referred to as a CT image.

To obtain a tomography image, a tomography imaging apparatus performs a tomography scan of an object to acquire raw data. The acquired raw data is used to reconstruct a tomography image. In this case, the raw data may be projection data obtained by projecting an X-ray onto the object or a projection data set called a sinogram.

For example, to obtain a CT image, image reconstruction may have to be performed using raw data obtained by performing a CT scan.

In detail, a CT scan is performed as an X-ray source included in a CT apparatus rotates around an object, and raw data is acquired from the CT scan. To produce a cross-sectional CT image, to acquire raw data, the X-ray source has to rotate by an angle that is greater than or equal to 180 or 360 degrees. If one period is defined as the time required to acquire raw data needed for reconstructing one cross-sectional CT image, one period in a general CT apparatus is greater than or equal to 0.2 seconds.

If an object to be scanned moves quickly, motion of the object may occur even during one period. Due to the motion of the object, motion artifacts may occur during reconstruction of a CT image.

Furthermore, a 3D CT image may be reconstructed using a plurality of cross-sectional CT images. Thus, motion of an object may occur very frequently during acquisition of raw data necessary for reconstructing a 3D CT image.

When motion artifacts occur, boundaries of an object in a reconstructed CT image may appear blurred, or a reconstructed image may be unclear. Thus, motion artifacts introduced in a CT image reduce the quality of the CT image and accordingly, degrade the accuracy of analysis of an image and diagnosis of a disease by a user, e.g., a medical practitioner.

Thus, for a CT scan of a moving object, it is of paramount importance to reconstruct a CT image having minimized motion artifacts.

SUMMARY

One or more exemplary embodiments include a tomography imaging apparatus and a method of reconstructing a tomography image whereby, during a tomography scan of a moving object, motion of the object may be measured accurately.

One or more exemplary embodiments include a tomography imaging apparatus and a method of reconstructing a tomography image, which are capable of effectively reducing motion artifacts that may be introduced in a reconstructed tomography image.

Additional aspects will be set forth in part in the description which follows and, in part, will be apparent from the description, or may be learned by practice of the presented exemplary embodiments.

According to one or more exemplary embodiments, a tomography imaging apparatus includes: a data acquisition unit configured to acquire a plurality of partial data respectively corresponding to a plurality of consecutive angular sections by performing a tomography scan on a moving object; and an image processing unit configured to measure global motion of the object and motion of a first region in the object based on the plurality of partial data, acquire first information representing motion of the object by reflecting the global motion in the motion of the first region, and reconstruct a final tomography image representing the object based on the first information.

The image processing unit may reconstruct the final tomography image by correcting the motion of the object in a tomography image representing the object based on the first information.

The image processing unit may compare two partial data respectively corresponding to two adjacent angular sections among the plurality of partial data with each other and acquire the first information based on a comparison result.

The image processing unit may compare two partial images respectively corresponding to the two adjacent angular sections and reconstructed according to a partial angle reconstruction (PAR) method with each other and acquire the first information based on a comparison result.

Each of the plurality of angular sections may have a value less than 180°.

The global motion may include at least one of translation and rotation of the object, and the motion of the first region may include motion that occurs due to characteristics of an organ or body part included in the first region.

The motion of the first region may include motion of a body part, which occurs in the first region due to at least one of respiration, heartbeat, and generation of a biological signal.

The image processing unit may acquire a plurality of partial tomography images respectively corresponding to the plurality of angular sections based on the plurality of partial data and acquire the first information based on a surface of the object imaged in the plurality of partial tomography images.

The image processing unit may mask at least one body part included in the object in each of the plurality of partial tomography images and measure motion of an edge included in the masked at least one body part as the global motion.

The image processing unit may mask a body part including at least one of ribs and vertebra in each of a plurality of partial tomography images.

The image processing unit may measure the global motion by using rigid registration.

The image processing unit may measure the motion of the first region by using non-rigid registration.

The image processing unit may reconstruct the final tomography image by primarily correcting the global motion of the object in a tomography image representing the object based on the first information and secondarily correcting the motion of the first region in the primarily corrected tomography image.

The tomography imaging apparatus may further include a display unit configured to display the final tomography image.

The tomography imaging apparatus may further include a communication unit configured to transmit the final tomography image to at least one of an external server, medical imaging apparatus, and computing device.

The image processing unit may generate second information including information about the motion of the object based on the first information.

The tomography imaging apparatus may further include a display unit configured to display a screen indicating the second information.

The second information may include an amount of the motion of the object classified into a plurality of stages.

The second information may include the type of the motion of the object.

The second information may include the motion of the object classified into a plurality of stages.

The second information may include information indicating whether rescanning is required based on an amount of the motion of the object.

The image processing unit may control an alarm signal notifying rescanning to be output when it is determined that the motion of the object occurs in an amount greater than or equal to a threshold value based on the first information.

According to one or more exemplary embodiments, a method of reconstructing a tomography image includes: acquiring a plurality of partial data respectively corresponding to a plurality of consecutive angular sections by performing a tomography scan on a moving object; measuring global motion of the object and motion of a first region in the object based on the plurality of partial data and acquiring first information representing motion of the object by reflecting the global motion in the motion of the first region; and reconstructing a final tomography image representing the object based on the first information.

The reconstructing of the final tomography image may include reconstructing the final tomography image by correcting the motion of the object in a tomography image representing the object based on the first information.

The acquiring of the first information may include comparing two partial data respectively corresponding to two adjacent angular sections among the plurality of partial data with each other and acquiring the first information based on a comparison result.

The global motion may include at least one of translation and rotation of the object, and the motion of the first region may include motion that occurs due to characteristics of an organ or body part included in the first region.

The motion of the first region may include motion of a body part, which occurs in the first region due to at least one of respiration, heartbeat, and generation of a biological signal.

In the acquiring of the first information, the global motion may be measured using rigid registration, and the motion of the first region may be measured using non-rigid registration.

BRIEF DESCRIPTION OF THE DRAWINGS

These and/or other aspects will become apparent and more readily appreciated from the following description of the exemplary embodiments, taken in conjunction with the accompanying drawings in which:

FIG. 12B is diagram for explaining partial data and a partial tomography image;

FIGS. 19A and 19B are diagrams for explaining reconstruction of a tomography image using a half reconstruction method;

DETAILED DESCRIPTION

Figure 1:
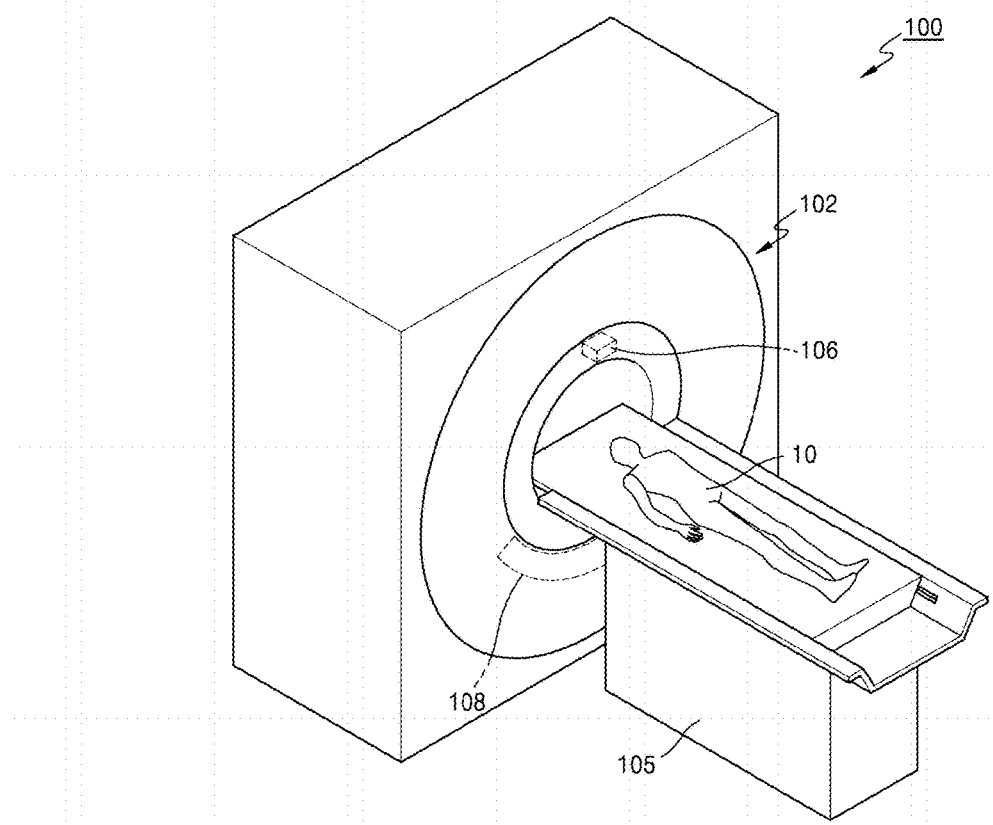
FIG. 1 is a schematic diagram of a computed tomography (CT) system according to an exemplary embodiment.

Advantages and features of one or more embodiments of the inventive concept and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the inventive concept will only be defined by the appended claims. Like reference numerals refer to like elements throughout the specification.

Hereinafter, the terms used in the specification will be briefly defined, and the embodiments will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the inventive concept means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail. As used herein, the term "and/or" includes any and all combinations of one or more of the associated listed items. Expressions such as "at least one of," when preceding a list of elements, modify the entire list of elements and do not modify the individual elements of the list. Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

Throughout the specification, a "CT image" may mean an image generated by synthesizing a plurality of X-ray images that are obtained by photographing an object while a CT imaging apparatus rotates around at least one axis with respect to the object.

Throughout the specification, an "object" may be a human, an animal, or a portion of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to the physical body.

Throughout the specification, a "user" may be, but is not limited to, a medical expert including a medical doctor, a nurse, a medical laboratory technologist, a medial image expert, or a technician who repairs a medical apparatus.

Since a CT system is capable of providing a cross-sectional image of an object, the CT system may distinctively express an inner structure, e.g., an organ such as a kidney or a lung, of the object, compared to a general X-ray imaging apparatus.

The CT system may obtain a plurality of pieces of image data with a thickness not more than 2 mm several hundred times per second and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to allow a user to easily observe an area of interest in volume rendering.

Voxel of interest (VOI)—a method of displaying only a selected area in volume rendering.

A CT system 100 according to an embodiment of the inventive concept will now be described with reference to FIGS. 1 and 2. The CT system 100 may include various types of devices.

FIG. 1 schematically illustrates the CT system 100. Referring to FIG. 1, the CT system 100 may include a gantry 102, a table 105, an X-ray generating unit 106, and an X-ray detecting unit 108.

The gantry 102 may include the X-ray generating unit 106 and the X-ray detecting unit 108.

An object 10 may be positioned on the table 105.

The table 105 may move in a predetermined direction (e.g., at least one of up, down, right, and left directions) during a CT imaging procedure. Also, the table 105 may tilt or rotate by a predetermined angle in a predetermined direction.

The gantry 102 may also tilt by a predetermined angle in a predetermined direction.

Figure 2:
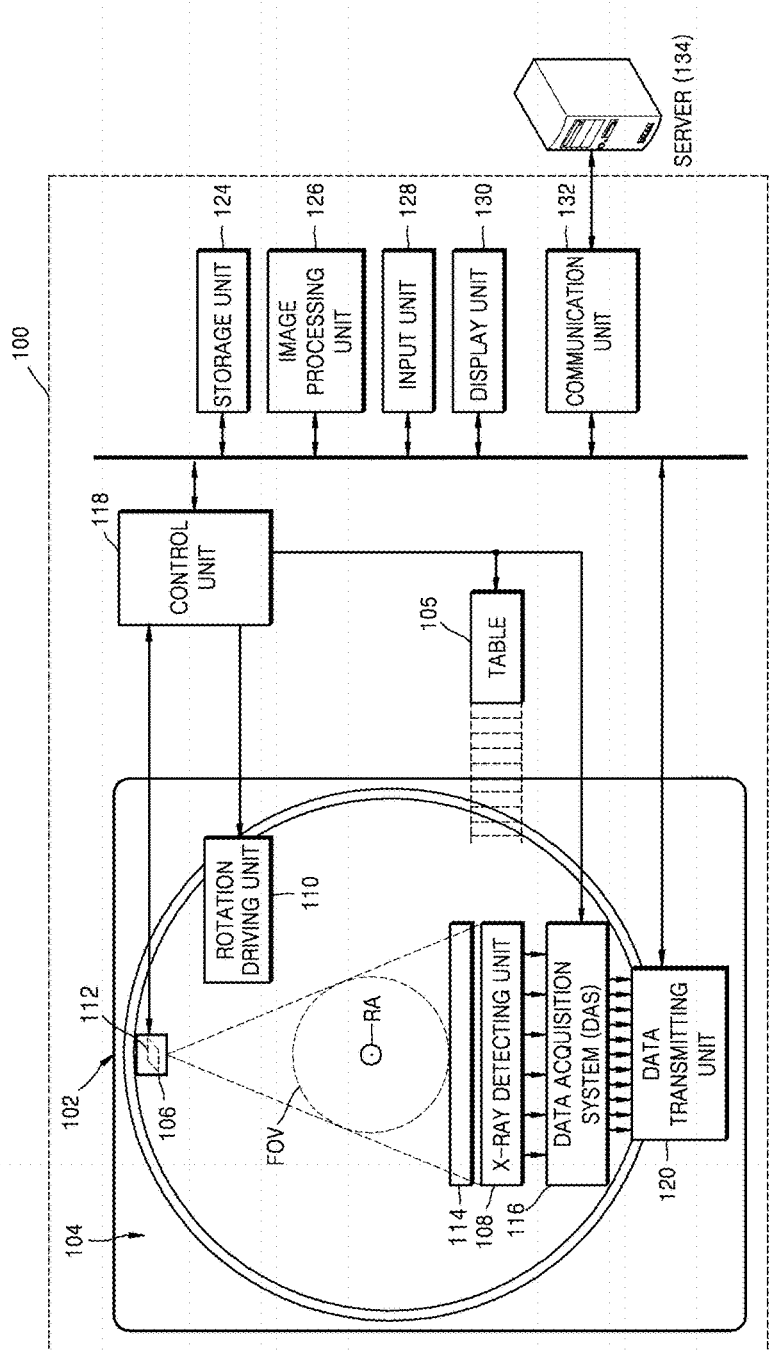
FIG. 2 is a block diagram of a structure of the CT system of FIG. 1.

FIG. 2 is a block diagram illustrating a structure of the CT system 100.

The CT system 100 may include the gantry 102, the table 105, a control unit 118, a storage unit 124, an image processing unit 126, an input unit 128, a display unit 130, and a communication unit 132.

As described above, the object 10 may be positioned on the table 105. In the present embodiment, the table 105 may move in a predetermined direction (e.g., at least one of up, down, right, and left directions), and movement of the table 105 may be controlled by the control unit 118.

The gantry 102 may include a rotating frame 104, the X-ray generating unit 106, the X-ray detecting unit 108, a rotation driving unit 110, a data acquisition system (DAS) 116, and a data transmitting unit 120.

The gantry 102 may include the rotating frame 104 having a loop shape capable of rotating with respect to a predetermined rotation axis RA. Also, the rotating frame 104 may have a disc shape.

The rotating frame 104 may include the X-ray generating unit 106 and the X-ray detecting unit 108 that are arranged to face each other so as to have predetermined fields of view FOV. The rotating frame 104 may also include an anti-scatter grid 114. The anti-scatter grid 114 may be positioned between the X-ray generating unit 106 and the X-ray detecting unit 108.

In a medical imaging system, X-ray radiation that reaches a detector (or a photosensitive film) includes not only attenuated primary radiation that forms a valuable image but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driving unit 110 and may rotate the X-ray generating unit 106 and the X-ray detecting unit 108 at a predetermined rotation speed. The rotating frame 104 may receive the driving signal and power from the rotation driving unit 110 while the rotating frame 104 contacts the rotation driving unit 110 via a slip ring (not shown). Also, the rotating frame 104 may receive the driving signal and power from the rotation driving unit 110 via wireless communication.

The X-ray generating unit 106 may receive a voltage and current from a power distribution unit (PDU) (not shown) via a slip ring (not shown) and then a high voltage generating unit (not shown), and may generate and emit an X-ray. When the high voltage generating unit applies a predetermined voltage (hereinafter, referred to as a tube voltage) to the X-ray generating unit 106, the X-ray generating unit 106 may generate X-rays having a plurality of energy spectra that correspond to the tube voltage.

The X-ray generated by the X-ray generating unit 106 may be emitted in a predetermined form due to a collimator 112.

The X-ray detecting unit 108 may be positioned to face the X-ray generating unit 106. Each of the plurality of X-ray detecting devices may establish one channel but one or more embodiments of the inventive concept are not limited thereto.

The X-ray detecting unit 108 may detect the X-ray that is generated by the X-ray generating unit 106 and that is transmitted through the object 10, and may generate an electrical signal corresponding to intensity of the detected X-ray.

The X-ray detecting unit 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detecting unit 108. Electrical signals generated by the X-ray detecting unit 108 may be acquired by the DAS 116. Electrical signals generated by the X-ray detecting unit 108 may be acquired by wire or wirelessly by the DAS 116. Also, the electrical signals generated by the X-ray detecting unit 108 may be provided to an analog-to-digital converter (not shown) via an amplifier (not shown).

According to a slice thickness or the number of slices, only some of a plurality of pieces of data collected by the X-ray detecting unit 108 may be provided to the image processing unit 126 via the data transmitting unit 120, or the image processing unit 126 may select only some of the plurality of pieces of data.

Such a digital signal may be provided to the image processing unit 126 via the data transmitting unit 120. The digital signal may be provided to the image processing unit 126 by wire or wirelessly.

The control unit 118 may control an operation of each of the elements in the CT system 100. For example, the control unit 118 may control operations of the table 105, the rotation driving unit 110, the collimator 112, the DAS 116, the storage unit 124, the image processing unit 126, the input unit 128, the display unit 130, the communication unit 132, or the like.

The image processing unit 126 may receive data acquired by the DAS 116 (e.g., raw data that is data before processing), via the data transmitting unit 120, and may perform pre-processing.

The pre-processing may include, for example, a process of correcting a sensitivity irregularity between channels and a process of correcting signal loss due to a rapid decrease in signal strength or due to the presence of an X-ray absorbing material such as metal.

Data output from the image processing unit 126 may be referred to as raw data or projection data. The projection data may be stored in the storage unit 124 with imaging conditions (e.g., the tube voltage, an imaging angle, etc.) during the acquisition of data.

The projection data may be a group of data values that correspond to the intensity of the X-ray that has passed through the object 10. For convenience of description, a group of a plurality of pieces of projection data that are simultaneously obtained from all channels at the same imaging angle is referred to as a projection data set.

The storage unit 124 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processing unit 126 may reconstruct a cross-sectional image of the object 10 by using the acquired projection data set. The cross-sectional image may be a 3D image. In other words, the image processing unit 126 may reconstruct a 3D image of the object 10 by using a cone beam reconstruction method or the like, based on the acquired projection data set.

The input unit 128 may receive an external input with respect to an X-ray tomography imaging condition, an image processing condition, or the like. For example, the X-ray tomography imaging condition may include tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, or the like. Also, the image processing condition may include a resolution of an image, an attenuation coefficient setting for the image, setting for an image combining ratio, or the like.

The input unit 128 may include a device for receiving a predetermined input from an external source. For example, the input unit 128 may include a microphone, a keyboard, a mouse, a joystick, a touch pad, a touch pen, a voice recognition device, a gesture recognition device, or the like.

The display unit 130 may display an X-ray image reconstructed by the image processing unit 126.

Exchanges of data, power, or the like between the aforementioned elements may be performed by using at least one of wired communication, wireless communication, and optical communication.

The communication unit 132 may perform communication with an external device, an external medical apparatus, etc. via a server 134 or the like. The communication will now be described with reference to FIG. 3.

Figure 3:
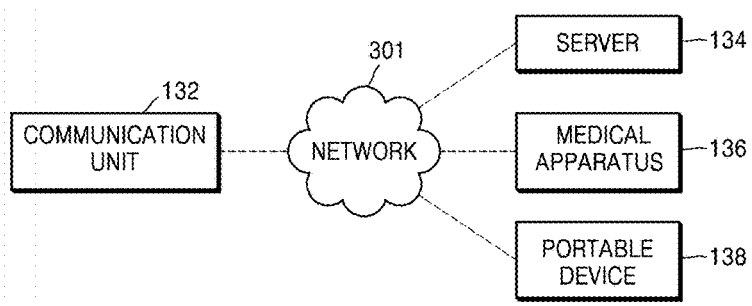
FIG. 3 is a block diagram of communication performed by a communication unit.

FIG. 3 is a block diagram illustrating the communication performed by the communication unit 132.

The communication unit 132 may be wiredly or wirelessly connected to a network 301 and therefore may perform communication with the server 134, a medical apparatus 136, or a portable device 138. The communication unit 132 may exchange data with a hospital server or other medical apparatuses in a hospital connected via a picture archiving and communication system (PACS).

Also, the communication unit 132 may perform data communication with the portable device 138 or the like, according to the digital imaging and communications in medicine (DICOM) standard.

The communication unit 132 may transmit and receive data related to diagnosing the object 10, via the network 301. Also, the communication unit 132 may transmit and receive a medical image obtained from the medical apparatus 136 such as a magnetic resonance imaging (MRI) apparatus, an X-ray apparatus, or the like.

Furthermore, the communication unit 132 may receive a diagnosis history or a medical treatment schedule about a patient from the server 134 and may use the diagnosis history or the medical treatment schedule to diagnose the patient. Also, the communication unit 132 may perform data communication not only with the server 134 or the medical apparatus 136 in a hospital but also with the portable device 138 of a user or patient.

Also, the communication unit 132 may transmit information about a device error, information about a quality control status, or the like to a system manager or a service manager via the network 301, and may receive a feedback regarding the information from the system manager or service manager.

As described above with reference to FIGS. 1 through 3, the image processing unit 126 may reconstruct a tomography image from raw data (e.g., projection data).

A method of reconstructing a tomography image from raw data acquired as the X-ray generating unit 106 rotates by an angle that is greater than or equal to 180° and less than 360° is hereinafter referred to as a half reconstruction method. A method of reconstructing a tomography image from raw data acquired as the X-ray generating unit 106 rotates by 360° is hereinafter referred to as a full reconstruction method. Furthermore, a method of reconstructing a tomography image from raw data acquired as the X-ray generating unit 106 rotates by less than 180° is hereinafter referred to as a partial angle reconstruction (PAR) method. A tomography image reconstructed using a half or full reconstruction method is a complete image showing the whole object, while a tomography image reconstructed using a PAR method is an incomplete image showing a part of the object. In this case, an incomplete image reconstructed using a PAR method is referred to as a 'partial image' or a 'partial angle image'.

According to an exemplary embodiment, to acquire a final tomography image, an object may be imaged using a half or full reconstruction method. Furthermore, a PAR method may be used to acquire first information indicating motion of an object.

In detail, as the time to acquire raw data needed to reconstruct a cross-sectional tomography image decreases, an image having reduced motion artifacts may be reconstructed. In other words, as the time to acquire raw data needed to reconstruct a cross-sectional tomography image decreases, temporal resolution may be increased and the amount of radiation on a patient may be decreased. Thus, a partial image obtained using a PAR method has a higher temporal resolution than a tomography image obtained using a half or full reconstruction method. Thus, according to an exemplary embodiment, by measuring motion of an object based on a partial image having a high temporal resolution, the motion of an object may be measured more accurately.

Figure 4:
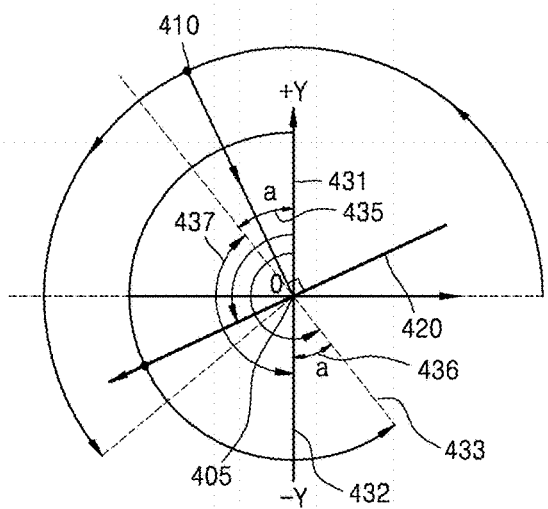
FIG. 4 is a diagram for explaining reconstruction of a tomography image using a half reconstruction method.

Referring to FIG. 4, if the X-ray generating unit 106 emits a cone beam having a fan shape that spreads out from a predetermined point, during half reconstruction, a tomography scan is performed by rotating the X-ray generating unit 106 by 180° plus twice a fan angle (fan angle x2), and a tomography image may be reconstructed from raw data acquired during an interval of 180° plus twice the fan angle (fan angle x2). Furthermore, if reconstruction is performed by converting a fan-shaped beam into a parallel beam or if the X-ray generating unit 106 emits a parallel beam, during half reconstruction, a tomography image may be reconstructed from raw data corresponding to an interval of 180° plus a fan angle. In other words, reconstructing a tomography image from raw data acquired using a cone beam further requires raw data corresponding to the fan angle, as compared to reconstructing a tomography image from raw data acquired using a parallel beam.

In detail, if a beam has a shape of a parallel beam instead of a cone beam, as described below with reference to FIG. 6B, an angle by which the X-ray generating unit 106 has to rotate more than 180° is less than twice a fan angle a for the cone beam, and the X-ray generating unit 106 may only rotate by one period of 180° plus the fan angle a. For example, if the fan angle a is 60°, tomography using a cone beam requires raw data acquired by rotating the X-ray generating unit 106 by an angular section of 300° (180°+2a), while tomography using a parallel beam requires raw data acquired by rotating the X-ray generating unit 106 by an angular section of 240° (180°+a). Thus, if the parallel beam is used, half reconstruction may be performed over one period of 180° plus the fan angle a (=240°).

FIG. 4 illustrates an example where half reconstruction is performed using raw data acquired using a parallel beam during an interval of 180° plus the fan angle a.

Referring to FIG. 4, when the X-ray generating unit 106 emits an X-ray towards an object 405 from a beam position 410, the X-ray detecting unit 108 detects the X-ray from a detection surface 420. The beam position 410 moves in a circle around the object 405 and rotates by one period of 180°+a. The detection surface 420 rotates by an angle corresponding to that of the beam position 410. In detail, the beam position 410 moves by an angle of 180° from a positive Y-axis to a negative Y-axis and then further by fan angle a to a position 433.

In half reconstruction, one tomography image may be reconstructed from pieces of projection data acquired over an initial angular section a 435, an intermediate angular section 437, and a last angular section a 436.

As the time to acquire raw data needed to reconstruct one tomography image decreases, an image having reduced motion artifacts may be reconstructed from the raw data.

Furthermore, as the time to acquire raw data needed to reconstruct one tomography image decreases, temporal resolution may be increased. Thus, if the X-ray generating unit 106 rotates at a constant velocity, a tomography image reconstructed using a half reconstruction method has a higher temporal resolution than a tomography image reconstructed using a full reconstruction method.

A tomography imaging apparatus according to an exemplary embodiment may reconstruct a final tomography image using the half reconstruction method described with reference to FIG. 4.

Furthermore, a tomography image reconstructed using a PAR method has a higher temporal resolution than a tomography image obtained using a half or full reconstruction method.

In a tomography imaging method according to an exemplary embodiment, motion of an object may be measured based on a plurality of pieces of partial data obtained using a PAR method. Each of the plurality of pieces of partial data is acquired using the PAR method, and a plurality of partial tomography images having a high temporal resolution may be obtained from the plurality of pieces of partial data. Using a plurality of partial tomography images having a high temporal resolution allows motion of an object with respect to time to be measured highly accurate. Furthermore, by reconstructing and outputting a final tomography image after compensating for motion of an object based on the measured motion of the object, a final tomography image having reduced motion artifacts may be obtained. In addition, a user, e.g., a medical practitioner, may diagnose an object easily and accurately by using the output final tomography image.

A tomography imaging apparatus according to an exemplary embodiment that outputs a final tomography image after motion of an object has been compensated for by accurately measuring the motion of the object will now be described in detail with reference to FIGS. 5 through 24.

Examples of a scan mode used for a tomography scan may include a prospective mode and a retrospective mode, as described in detail with reference to FIGS. 5A and 5B. Furthermore, a tomography imaging apparatus according to an exemplary embodiment may perform a tomography scan according to various scan methods. Examples of scan methods used for a tomography scan may include axial and helical scan methods.

Figure 5A:
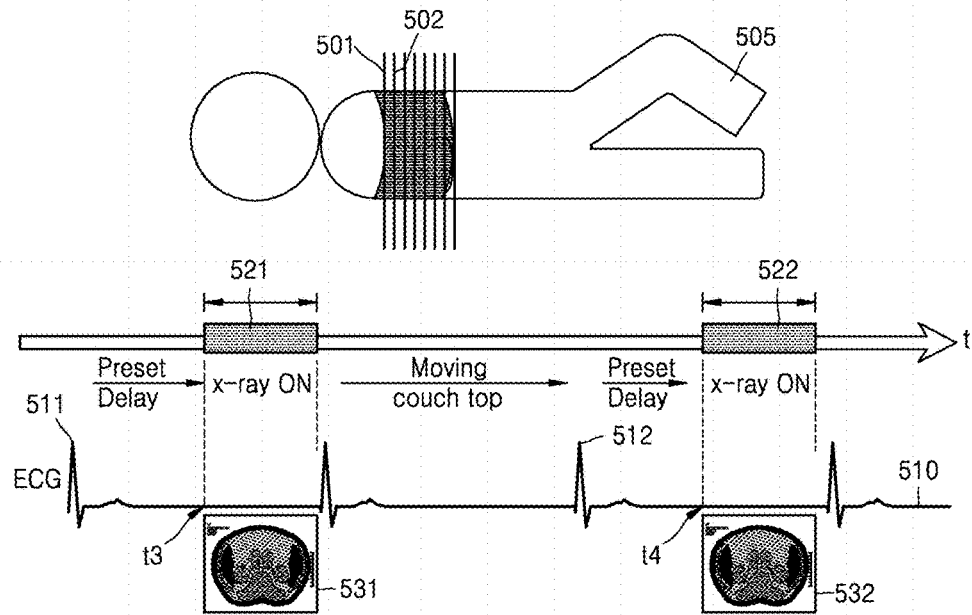
FIGS. 5A and 5B illustrate scan modes that are applied to a tomography scan.
Figure 5B:
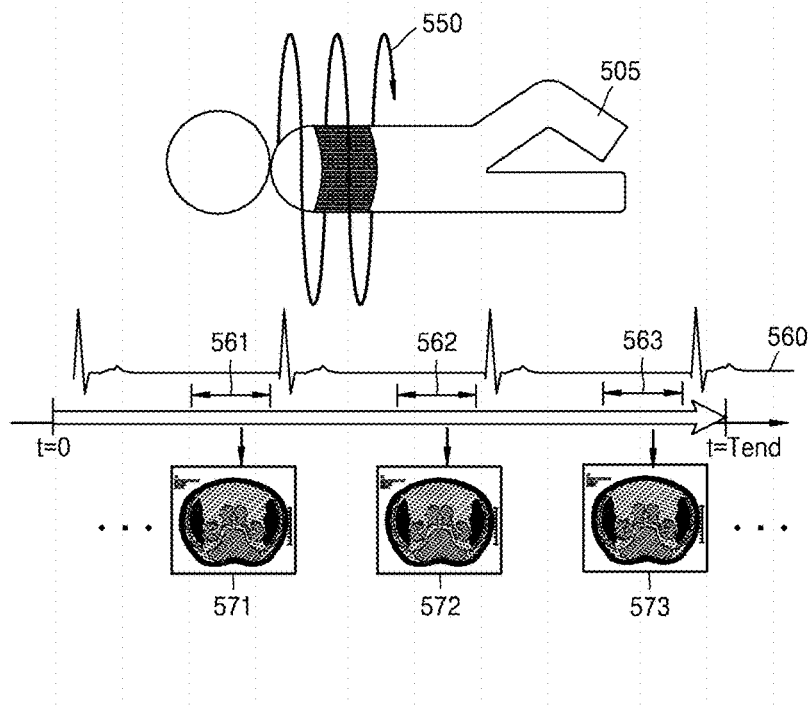

FIGS. 5A and 5B illustrate scan modes and scan methods that are applied to a tomography scan. In detail, FIG. 5A illustrates a tomography scan performed using an axial scan method in a prospective mode, and FIG. 5B illustrates a tomography scan performed using a helical scan method in a retrospective mode.

Scan modes may be classified depending on whether a cardiac cycle in a patient being scanned is regular or not. Furthermore, electrocardiogram (ECG) gating may be used to acquire raw data necessary for image reconstruction. FIG. 5A illustrates an example where a tomography scan is performed as the table (105 of FIG. 2) moves in an axial direction of a patient 505.

Referring to FIG. 5A, in an axial scan method that is one of the tomography scanning techniques, when the table 105 is stationary, an axial scan is performed by emitting X-rays on the patient 505, and after the table 105 is moved by a predetermined distance 501-502, raw data is acquired by emitting X-rays on the patient 505 during a predetermined interval 522. A tomography imaging apparatus according to an exemplary embodiment may perform a tomography scan by using an axial scan method to acquire a plurality of pieces of partial data. Furthermore, the tomography imaging apparatus may acquire raw data needed for reconstructing a final tomography image by using an axial scan method.

Furthermore, referring to FIG. 5A, for a person having a regular cardiac cycle, a prospective mode is used to regularly gate an ECG signal 510. In the prospective mode, a predetermined interval 521 is automatically selected, the predetermined interval 521 starting at a time point t3 that is a predetermined time after an R peak 511. Raw data is acquired by irradiating X-rays onto the patient 505 during the predetermined interval 521. Then, the predetermined interval 522 is automatically selected, the predetermined interval 522 starting at a time point t4 that is a predetermined time after a subsequent R peak 512. In this case, when the table 105 is stationary, scanning is performed by emitting X-rays, and after the table 105 is moved by a predetermined distance 501-502, raw data is acquired by emitting X-rays during the predetermined interval 522. A technique for performing scanning as the table 105 moves at predetermined intervals along an axial direction of the patient 505, as shown in FIG. 5A, is referred to as an axial reconstruction method. In detail, among half reconstruction methods, a technique for performing scanning as the table 105 moves along an axial direction of the patient 505, as shown in FIG. 5A, is referred to as an axial half reconstruction method. An axial half reconstruction method may be used by a tomography imaging apparatus according to an exemplary embodiment.

A data acquisition unit (710 of FIG. 7) reconstructs tomography images 531 and 532 respectively from raw data acquired during the predetermined intervals 521 and 522.

Referring to FIG. 5B, a helical scan method is a tomography scanning technique for performing a scan by continuously emitting X-rays as the table 105 moves for a predetermined time from t=0 to t=end. In detail, the table 105, on which a patient 505 including an object is placed, is continuously moved at a constant velocity for a predetermined time, and a scan is performed by continuously emitting X-rays toward the patient 505 during movement of the table 105. As the scan continues, a trajectory 550 along which an X-ray light source moves has a helical shape.

Furthermore, referring to FIG. 5B, If the patient 505 has arrhythmia and thus suffers from an irregular cardiac cycle, the cardiac cycle cannot be detected regularly as in a prospective mode due to low regularity of the cardiac cycle. In this case, a retrospective mode is used to irregularly gate an ECG signal 560. In the retrospective mode, raw data is acquired during the entire cardiac cycle or a continuous range of the cardiac cycle of the ECG signal 560 by emitting X-rays toward the patient 505, and then partial intervals 561 through 563 are respectively selected for reconstruction of tomography images 571 through 573. In other words, in the retrospective mode, after the user individually sets the partial intervals 561 through 563 used for image reconstruction to detect the partial intervals 561 through 563, raw data acquired during the detected partial intervals 561 through 563 may be used to reconstruct the tomography images 571 through 573, respectively.

In detail, in the retrospective mode, a tomography scan is performed by continuously emitting X-rays for a predetermined time ranging from t=0 to t=end. Furthermore, the tomography scan may be performed with continuous movement of the table 105 at a constant velocity. In this case, the trajectory 550 in which an X-ray light source moves has a helical shape.

A technique for performing a scan by continuously emitting X-rays while the table 105 is being moved so that the trajectory 550 has a helical shape, as shown in FIG. 5B, is referred to as a helical reconstruction method. In detail, among half reconstruction methods, a technique for performing scanning by continuously emitting X-rays while the table 105 is being moved, as shown in FIG. 5B, is referred to as a helical half reconstruction method. The helical half reconstruction method may be used by a tomography imaging apparatus according to an exemplary embodiment.

For example, for a patient having an irregular cardiac cycle, a tomography scan may be performed in a retrospective mode by using a helical scan method. Furthermore, for a patient having a regular cardiac cycle, a tomography scan may be performed in a prospective mode by using an axial scan method. However, exemplary embodiments are not limited thereto, and a tomography scan may be performed in a prospective mode by using a helical scan method or in a retrospective mode by using an axial scan method.

A tomography imaging apparatus according to an exemplary embodiment may acquire a plurality of pieces of partial data by performing a tomography scan using a helical scan method. Furthermore, the tomography imaging apparatus may acquire raw data necessary for reconstructing a final tomography image by using a helical scan method.

Figure 6A:
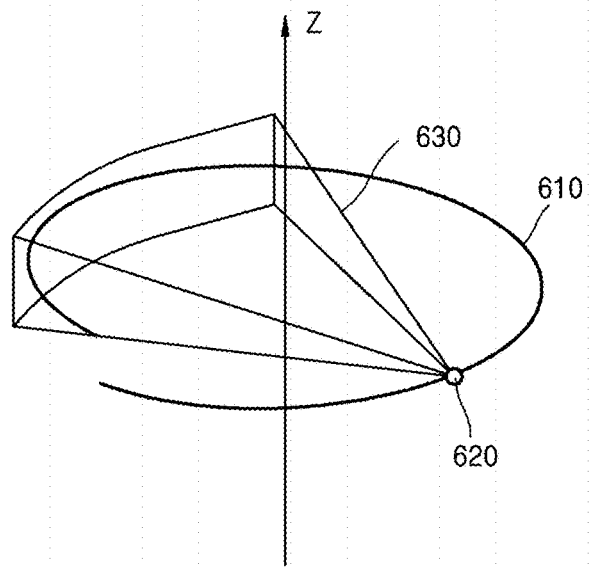
FIGS. 6A and 6B illustrate shapes of X-ray beams emitted toward an object.
Figure 6B:
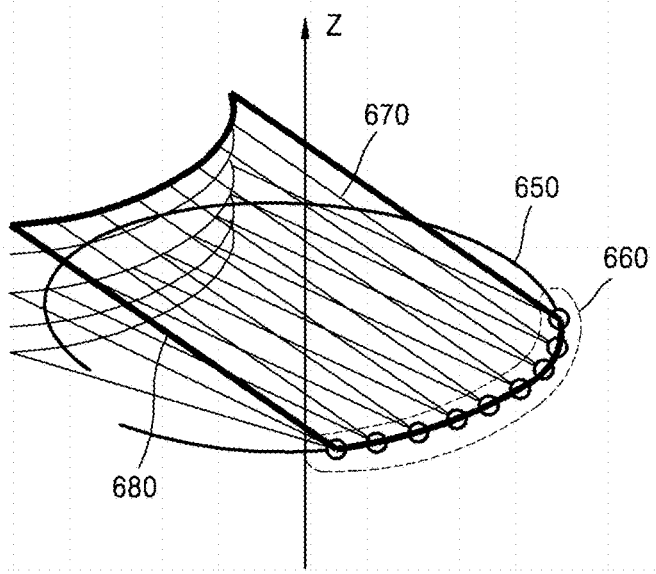

FIGS. 6A and 6B illustrate shapes of X-ray beams emitted toward an object. In detail, FIG. 6A illustrates an example where the X-ray generating unit 106 emits X-rays in a form of a cone beam, and FIG. 6B illustrates an example where the X-ray generating unit 106 emits X-rays in a form of a parallel beam.

Referring to FIG. 6A, when the X-ray generating unit 106 emits an X-ray at a predetermined position 620 while moving along a trajectory 610, the X-ray is irradiated onto the object in a cone shape 630.

Referring to FIG. 6B, when the X-ray generating unit 106 emits an X-ray at a predetermined position 660 while moving along a trajectory 650, the X-ray is irradiated onto the object in a parallel plane shape 670.

As shown in FIG. 6B, if the X-ray generating unit 106 emits X-rays in a form of a cone beam, X-ray beams emitted in a cone shape may be rearranged to arrange beams in parallel on a plane 680 that connects rows in the X-ray detecting unit 108 with the trajectory 650. In other words, a cone beam may be converted into a pseudo parallel-beam for image reconstruction. Furthermore, if a cone beam is converted into a parallel beam for image reconstruction, raw data is acquired as the X-ray generating unit 106 further rotates the fan angle "a", compared to a parallel beam. In detail, if the fan angle is "a", the X-ray generating unit 106 emitting a cone beam uses the raw data acquired during an angular section of 180°+2a, to acquire raw data corresponding to the angular section of 180°+a corresponding to the rebinned parallel beam.

As described with reference to FIGS. 6A and 6B, a tomography imaging apparatus according to an exemplary embodiment may be applied to a cone-beam tomography imaging apparatus or parallel-beam tomography imaging apparatus.

For convenience of explanation, an angular section during which the X-ray generating unit 106 rotates in order to acquire projection data needed for reconstructing a cross-sectional tomography image is hereinafter referred to as 'one period of angular sections'. For example, in a half reconstruction method, one period of angular sections may be greater than or equal to 180°. In a full reconstruction method, one period of angular sections may be 360°.

Figure 7:
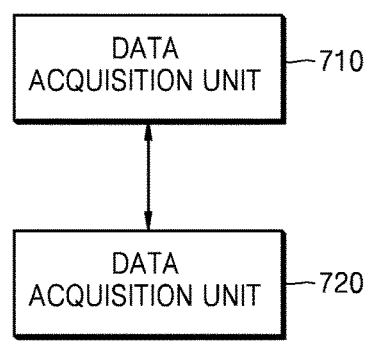
FIG. 7 is a block diagram of a tomography imaging apparatus according to an exemplary embodiment.

FIG. 7 is a block diagram of a tomography imaging apparatus 700 according to an exemplary embodiment.

Referring to FIG. 7, the tomography imaging apparatus 700 according to the present exemplary embodiment includes a data acquisition unit 710 and an image processing unit 720.

The tomography imaging apparatus 700 may be included in the CT system 100 described with reference to FIGS. 1 and 2. Furthermore, the tomography imaging apparatus 700 may be included in the medical apparatus 136 or the portable device 138 and thus connect to the CT system 100 and operate. In detail, the tomography imaging apparatus 700 may be any medical imaging apparatuses adapted to reconstruct an image from data acquired using a ray that has passed through an object. In other words, the tomography imaging apparatus 700 may be any medical imaging apparatus reconstructing a tomography image from projection data acquired using a ray that has passed through an object. In detail, the tomography imaging apparatus 700 may be a CT apparatus, an optical coherence tomography (OCT) apparatus, or positron emission tomography (PET)-CT apparatus. Thus, a tomography image acquired by the tomography imaging apparatus 700 may be a CT image, an OCT image, or a PET image. It is assumed hereinafter that the tomography image is a CT image. Furthermore, if the tomography imaging apparatus 700 is included in the CT system 100 described with reference to FIGS. 1 and 2, the acquisition unit 710 and the image processing unit 720 may be respectively include the gantry 102 and the image processing unit 126 shown in FIG. 2. Thus, descriptions of the tomography imaging apparatus 700 that are already provided above with respect to FIGS. 1 and 2 are omitted.

Referring to FIG. 7, the data acquisition unit 710 acquires a plurality of pieces of partial data. In this case, the plurality of pieces of partial data respectively correspond to a plurality of consecutive angular sections and are acquired by performing a tomography scan of a moving object. In detail, when a tomography scan is performed as the X-ray generating unit 106 rotates around an object, the X-ray detecting unit 108 and the DAS 116 detect X-rays that have passed through the object to acquire a plurality of pieces of partial data respectively corresponding to a plurality of consecutive partial angular sections.

The data acquisition unit 710 may receive a plurality of pieces of partial data from the outside. For example, if the tomography imaging apparatus 700 is connected to an external CT system (not shown), the server 134, the medical apparatus 136, or the portable device 138 via a wired or wireless communication network, the data acquisition unit 710 may receive the plurality of pieces of partial data from the external CT system, the server 134, the medical apparatus 136, or the portable device 138.

Furthermore, if the data acquisition unit 710 includes the gantry 102 described with reference to FIG. 2, the data acquisition unit 710 may acquire a plurality of pieces of partial data by performing a tomography scan. Each of the plurality of pieces of partial data may be raw data. In this case, the raw data may be projection data obtained by projecting radiation, e.g., X-rays onto the object or a projection data set called a sinogram.

Furthermore, the raw data may be a tomography image produced by performing filtered backprojection (FBP) on projection data or a sinogram. In detail, if the X-ray generating unit 106 emits an X-ray toward an object at a predetermined position, a viewpoint from which or direction in which the X-ray generating unit 106 faces the object is termed a view. Projection data means raw data acquired for each view, and a sinogram refers to raw data obtained by sequentially arranging a plurality of pieces of projection data respectively corresponding to a plurality of views For example, when a tomography scan is performed as the X-ray generating unit 106 emits X-rays toward an object at a point where the X-ray generating unit 106 moves by an interval of 2°, the point where the X-ray generating unit 106 emits the X-rays toward the object is referred to as a view. For example, during an angular section of 180°, as the X-ray generating unit 106 emits X-rays at each of 90 views, 90 pieces of projection data respectively corresponding to the 90 views are acquired. A sinogram corresponding to an angular section of 180° may be obtained by sequentially arranging the 90 pieces of projection data. A plurality of pieces of partial data will be described in more detail below with reference to FIGS. 11 through 13.

The image processing unit 720 measures global motion of an object and motion of a first region included in the object based on a plurality of pieces of partial data acquired by the data acquisition unit 710. The image processing unit 720 also acquires first information representing motion of the object by reflecting the global motion of the object in the motion of the first region. Furthermore, the image processing unit 720 outputs a final tomography image that represents the object based on the first information.

In this case, the global motion of the object may include at least one of rotation and translation of the entire object. Furthermore, the first region may be a part of the object, an organ included in the object, a specific portion or tissue to be examined or observed for diagnosis, or a portion set for examination or observation. Alternatively, the first region may be an internal organ included in the object. For example, if the first region is an abdominal cross-section, a region including an organ included in the abdomen may be set as the first region.

For example, the first region may be a region of interest (ROI) set by the user. Furthermore, the first region may be an organ to be examined for diagnosis of disease, such as at least one of lungs, the heart, the abdomen, the uterus, the brain, a breast, and the liver. In this case, the image processing unit 720 may extract an organ to be examined from a tomography image by automatically performing segmentation and set the extracted organ as the first region. In detail, the image processing unit 720 may set or extract the first region in or from a tomography image reconstructed from raw data, which is a tomography image before undergoing motion correction.

The motion of the first region may be motion that occurs due to characteristics of an organ or body part included in the first region. For example, if the first region includes the heart, the motion of the first region may be motion that occurs due to the heartbeat, contraction or expansion of blood vessels included in the heart, etc. As another example, if the first region includes the lungs, the motion of the first region may include expansion or contraction of the lungs that occurs during breathing. Furthermore, the motion of the first region may include motion caused by a biological signal, which occurs in a body part included in the first region.

In detail, the motion of the first region may include not only at least one of rotation and translation but also contraction, expansion, or deformation. For example, if the object is the heart and the first region is the coronary artery, a state of the coronary artery may change as the entire surface forming the coronary artery contracts, expands, and/or deforms. In this case, the state change includes a change in at least one of a size, a shape, a position, and a form of the coronary artery. As another example, if the object is the abdomen and the first region is a lung, a shape of the lung may change as the whole lung contracts or expands during respiration.

The image processing unit 720 measures both the global motion of the object and motion of the first region and acquires first information representing motion of the object including the global motion of the object and the motion of the first region. The image processing unit 720 may also perform motion correction of the moving object based on the first information, thereby reconstructing a final tomography image having reduced motion artifacts. In this case, the first information may represent motion of the object over time, i.e., motion of the object during the entire time interval corresponding to a plurality of consecutive angular sections.

Since the first information is obtained by measuring both the global motion of the object and motion of the first region that is a region of the object that is selected by the user for diagnosis, the first information indicates motion of the object including the global motion of the object as well as the motion of the first region. In other words, the motion of the first region may be measured accurately by reflecting the global motion of the object.

The image processing unit 720 may reconstruct a final tomography image by correcting motion of an object in a tomography image reconstructed from raw data based on the first information. In detail, the image processing unit 720 may predict a state of motion of the object at a first time point included in the entire time interval based on the first information, and correct the motion of the object based on the predicted state of the motion of the object, thereby reconstructing a final tomography image. In this case, the first time point is a time point when the final tomography image is to be reconstructed. The final tomography image may show the state of the object at the first time point. Furthermore, the first time point may be a time point corresponding to a predetermined view or a predetermined angle included in a plurality of consecutive angular sections.

In detail, the image processing unit 720 may reconstruct the final tomography image by performing motion correction on a tomography image that does not undergo motion correction, based on the first information.

Figure 8:
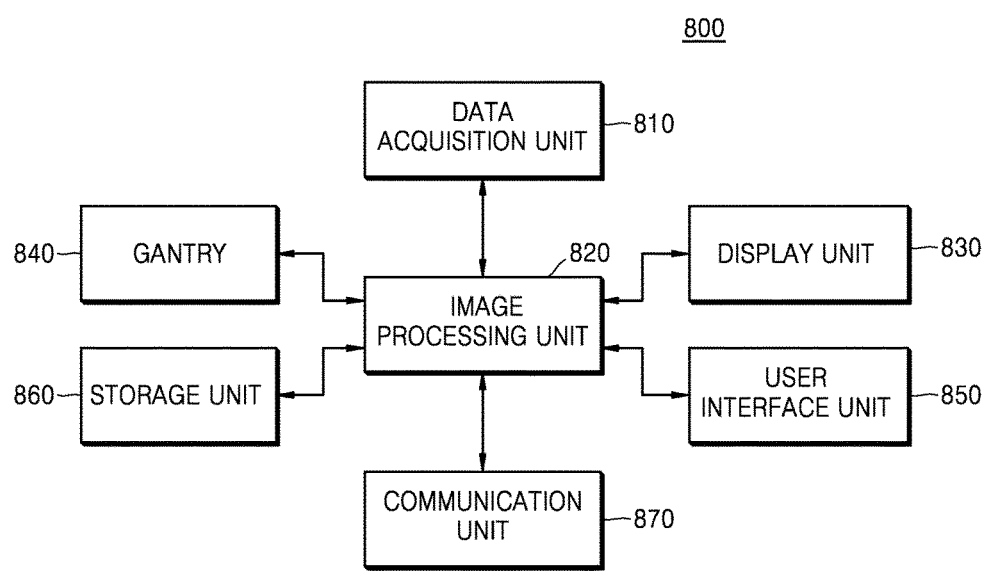
FIG. 8 is a block diagram of a tomography imaging apparatus according to another exemplary embodiment.

FIG. 8 is a block diagram of a tomography imaging apparatus 800 according to another exemplary embodiment.

Referring to FIG. 8, the tomography imaging apparatus 800 according to the present exemplary embodiment includes a data acquisition unit 810 and an image processing unit 820 that respectively correspond to the data acquisition unit 710 and the image processing unit 720 shown in FIG. 7. Descriptions that are already provided above with respect to FIG. 7 are omitted.

The tomography imaging apparatus 800 may further include a display unit 830, a gantry 840, a user interface unit 850, a storage unit 860, and a communication unit 870. Since the display unit 830, the gantry 840, the user interface unit 850, the storage unit 860, and the communication unit 870 have the same configurations and functions as those of their counterparts in the CT system 100 of FIG. 2, i. e., the display unit 130, the gantry 102, the input unit 128, the storage unit 124, and the communication unit 132, the same descriptions as those already provided with respect to FIG. 2 are omitted.

Referring to FIG. 8, the data acquisition unit 810 acquires a plurality of pieces of partial data.

The image processing unit 820 measures global motion of an object and motion of a first region included in the object based on a plurality of pieces of partial data acquired by the data acquisition unit 810. The image processing unit 820 also acquires first information representing motion of the object by reflecting the global motion of the object in the motion of the first region. Furthermore, the image processing unit 820 outputs a final tomography image that represents the object based on the first information.

In this case, the first information may be information representing motion of a surface forming the object including the first region. In detail, the first information may indicate the amount of motion of the first region having the global motion of the object. The global motion of the object includes at least one of rotation and translation of the object.

The display unit 830 displays a predetermined screen. In detail, the display unit 830 may display a user interface screen necessary for performing a tomography scan, or a reconstructed tomography image.

In detail, the display unit 830 may display a motion-corrected final tomography image. The display unit 830 may also display a screen including a tomography image before the motion correction and a motion-corrected final tomography image.

Furthermore, the display unit 830 may display a screen showing first information. The display unit 830 may also display a user interface screen. The user may perform various setting operations and data entry via the user interface screen output via the display unit 730.

In detail, the display unit 830 may display a screen showing a result obtained by quantifying measured global motion of the object and the amount of motion of the first region. The display unit 830 may also display a user interface screen representing at least one of the type and magnitude of motion of the object. Furthermore, when the amount of motion of the object is greater than or equal to a predetermined threshold, the display unit 830 may display a user interface screen including an alarm message that guides the user to perform image reconstruction or a tomography scan again.

In detail, the image processing unit 820 may generate second information including information about motion of the object based on the first information. In this case, the second information may be generated based on the first information and indicate the type, amount, or allowable range of motion of the object. A user interface screen including at least one piece of the first and second information generated by the image processing unit 820 may be output via the display unit 830.

Furthermore, the display unit 830 may be any type of devices that allow the user to visually recognize predetermined data. The display unit 830 may include a cathode ray tube (CRT) display, a liquid crystal display (LCD), a plasma display panel (PDP) display, an organic light-emitting diode (OLED) display, a field emission display (FED), an LED display, a vacuum fluorescent display (VFD), a digital light processing (DLP) display, a flat panel display (FPD), a 3D display, a transparent display, etc.

The gantry 840 includes the X-ray generating unit (106 of FIG. 2), the X-ray detecting unit (108 of FIG. 2), and the DAS (116 of FIG. 2) 116. The gantry 840 emits an X-ray toward an object, detects the X-ray that has passed through the object, and generates raw data corresponding to the detected X-ray.

In detail, the X-ray generating unit 106 produces an X-ray and emits the X-ray toward the object as the X-ray generating unit 106 rotates around the object. The X-ray detecting unit 108 then detects the X-ray that has passed through the object. The DAS 116 generates raw data corresponding to the detected X-ray. In this case, the raw data may be projection data obtained by projecting radiation onto the object or a projection data set called a sinogram.

The tomography imaging apparatus 800 according to the present exemplary embodiment may use any of a PAR method, a full reconstruction method, and a half reconstruction method to acquire first information and reconstruct a final tomography image.

In detail, the gantry 840 may perform a tomography scan by using at least one of a half reconstruction method, a full reconstruction method, and a PAR method, thereby acquiring raw data. The data acquisition unit 810 reconstructs a tomography image from raw data that is transmitted by the gantry 840 or an externally connected tomography system.

Furthermore, the image processing unit 820 may acquire first information by using a PAR method. The image processing unit 820 may also reconstruct a final tomography image by using a half or full reconstruction method.

The user interface unit 850 creates and outputs a user interface screen for receiving a predetermined command or data from a user and receives the predetermined command or data from the user via the user interface screen. The user interface screen output from the user interface unit 850 may also be output to the display unit 830 that may in turn display the user interface screen. The user may then view the user interface screen displayed via the display unit 830 to recognize predetermined information and input a predetermined command or data For example, the user interface unit 850 may include a mouse, a keyboard, or another input device including hard keys for inputting predetermined data. For example, the user may enter predetermined data or a command by manipulating at least one of the mouse, the keyboard, and the other input device in the user interface unit 850.

Furthermore, the user interface unit 850 may be formed as a touch pad. In detail, the user interface unit 850 includes a touch pad (not shown) combined with a display panel (not shown) in the display unit 830 and outputs a user interface screen to the display panel. When a predetermined command is input via the user interface screen, the touch pad may detect the input of the predetermined command to recognize the predetermined command input by the user.

In detail, if the user interface unit 850 is formed as a touch pad, when the user touches a predetermined point on the user interface screen, the user interface unit 850 detects a touched point. The user interface unit 850 may then transmit information about the detected touched point to the image processing unit 820. The image processing unit 820 may then recognize a user request or command corresponding to a menu item displayed at the detected point and generate a tomography image according to the recognized user request or command.

Alternatively, the user interface screen may be generated by the image processing unit 820.

Furthermore, the storage unit 860 may store data acquired by performing a tomography scan. In detail, the storage unit 860 may store at least one of raw data, i.e., projection data and a sinogram. Furthermore, the storage unit 860 may store various data, programs, etc., necessary for reconstructing a tomography image, as well as a finally reconstructed tomography image. The storage unit 860 may also store various data necessary for acquiring first information and acquired first information. (In detail, the storage unit 860 may store a plurality of pieces of partial data respectively acquired during a plurality of consecutive angular sections. In addition, the storage unit 860 may store second information acquired based on the first information.

Furthermore, the storage unit 860 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The communication unit 870 may perform communication with an external device, an external medical apparatus, etc. For example, the communication unit 870 may be connected to an external tomography system, a tomography apparatus, a server, or the like. Since the communication unit 870 may correspond to the communication unit 132 described with reference to FIG. 3, the same descriptions that are already provided above with respect to FIG. 3 are omitted.

The communication unit 870 may be connected to the network (301 of FIG. 3) by wire or wirelessly to communicate with external devices such as the server (134 of FIG. 3), the medical apparatus (136 of FIG. 3), or the portable device (138 of FIG. 3).

The communication unit 870 may receive a plurality of pieces of partial data necessary for acquiring first information via the network 301. Furthermore, the communication unit 870 may receive raw data necessary for reconstructing a final tomography image.

Furthermore, the communication unit 870 may receive a patient's diagnosis history or treatment schedule from the server 134 and use the same for clinical diagnosis of disease in the patient. The communication unit 870 may also perform data communication not only with the server 134 or the medical apparatus 136 in a hospital, but also with the portable device 138 held by a user or patient.

As described above, the communication unit 870 may transmit at least one of a final tomography image, first information, and second information generated by the image processing unit 820 to the server 134 or the medical apparatus 136 connected via the network 301. The at least one of the final tomography image, the first information, and the second information may be processed, used, or displayed by an external hospital or the like.

Operations of the tomography imaging apparatuses 700 and 800 according to the exemplary embodiments will now be described in more detail with reference to FIGS. 9 through 24. For convenience of explanation, the operation of the tomography imaging apparatus 800 is described.

Figure 9:
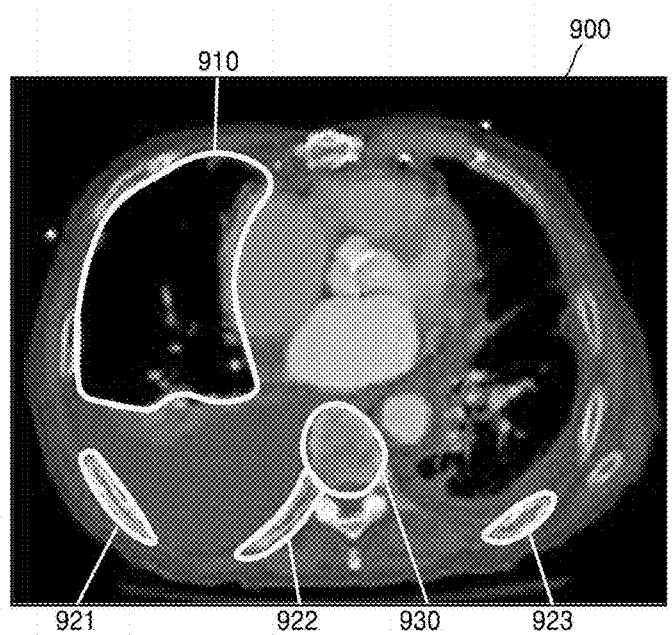
FIG. 9 illustrates a CT image obtained by scanning an object.

FIG. 9 illustrates a CT image 900 obtained by scanning an object.

It is hereinafter assumed that the CT image 900 is used as a tomography image used and processed by the tomography imaging apparatus 800 (700).

Referring to FIG. 9, the CT image 900 is a 2D tomography image showing a cross-section of a patient's abdomen. In the CT image 900, organs and tissues such as bones in the abdomen are shown, a lung 910 is shown on the left side thereof, and ribs 921 through 923 and vertebra 930 are shown around an outer edge of the abdominal cross-section that is an object. In the patient's abdomen, motion of the lung 910 may occur due to breathing, which causes motion artifacts in the lung 910. Motion artifacts are caused by not only motion of an organ or tissue included in the object to be scanned but also motion of the patient himself that is unrelated to the motion of the organ or tissue. In this case, the motion of the patient himself may mean motion of the object as a whole such as rotation and/or translation of a patient's body. For example, if the patient moves his or her abdomen to one side or turn his or her body to rotate the abdomen, the object may move as a whole.

Motion that occurs in a first region due to motion of an organ or tissue itself included in the object is hereinafter referred to as 'motion of the first region'. Motion that occurs when the object moves as a whole without regard to the motion of the organ or tissue itself included in the object is hereinafter referred to as 'global motion'.

For compensation for motion artifacts, it is necessary to accurately measure the amount of motion reflecting both motion of the first region and the global motion within the object, and correct motion of the object based on the measured amount of motion before reconstructing a final tomography image.

The motion of the first region may be measured by measuring motion of a region that is set in the object or obtained by segmenting the object. Furthermore, the global motion may be measured by measuring motion of an outer edge of the object or bones constituting the object.

In detail, if the first region includes the lung 910, the image processing unit 820 may measure motion of the first region by measuring motion of the lung 910.

Figure 10:
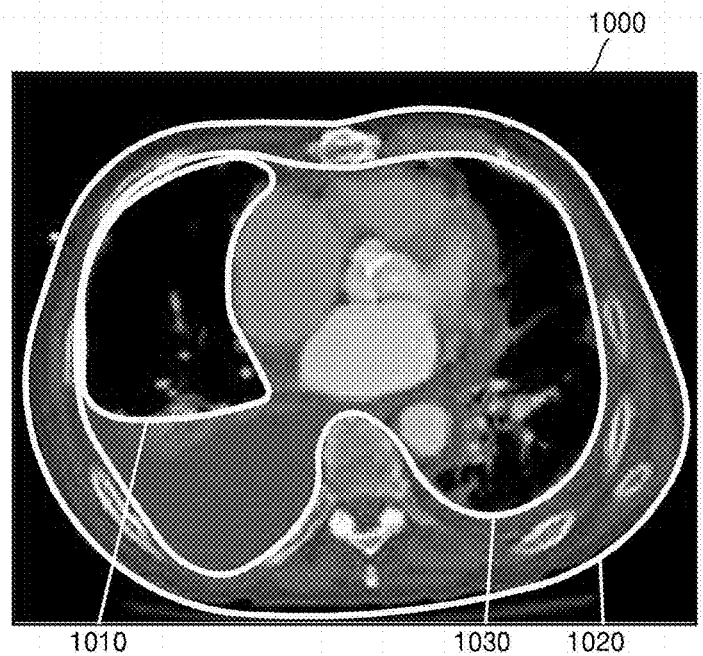
FIG. 10 is a diagram for explaining motion of an object.

If the object is the abdomen, the image processing unit 820 may measure the global motion by measuring motion of an outer edge of the object or a bone structure including at least one of the ribs 921 through 923 and the vertebra 930 that constitute the object FIG. 10 is a diagram for explaining motion of an object.

Referring to FIG. 10, if the object is the abdomen, the image processing unit 820 may obtain the amount of the global motion over time by detecting at least one of an inner edge 1010, an outermost edge 1030, and the bone structure described with reference to FIG. 9, which are formed by a surface of the object, in a tomography image 1000, and measuring the amount of motion of the detected at least one of the inner edge 1010, the outermost edge 1030, and the bone structure with respect to time.

Furthermore, if a lung is set as a first region, the image processing unit 820 may obtain the amount of motion of the first region over time by extracting a surface of the object that forms an edge of the lung from the tomography image 1000 and measuring the amount of motion of the extracted surface with respect to time.

An operation of acquiring first information based on measurement of the global motion and motion of the first region in the image processing unit 820 will now be described in more detail with reference to FIGS. 11 through 16.

Figure 11:
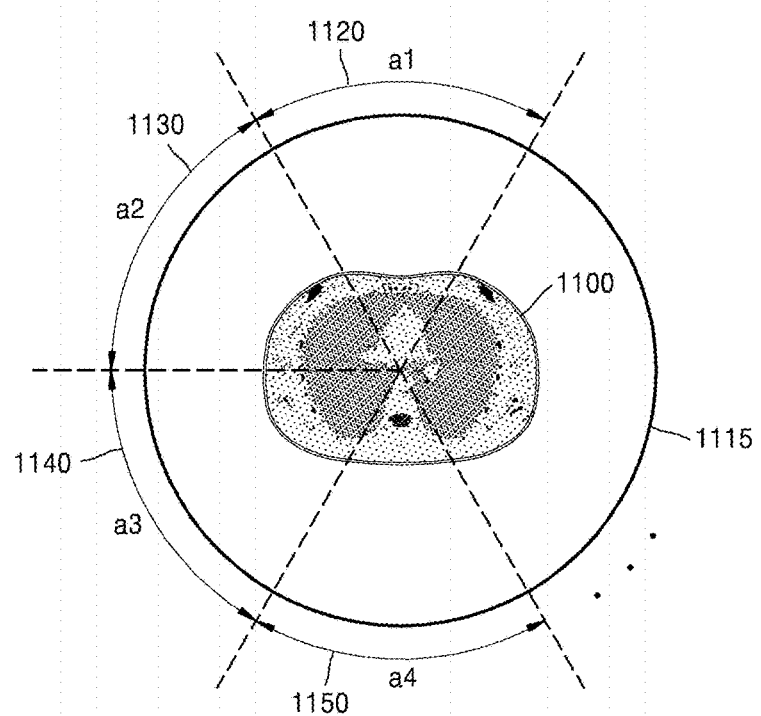
FIG. 11 is a diagram for explaining measurement of motion of an object.

FIG. 11 is a diagram for explaining measurement of motion of an object.

The image processing unit 820 may compare two pieces of partial data respectively corresponding to two adjacent angular sections among a plurality of pieces of partial data and acquire first information based on a comparison result.

Referring to FIG. 11, a plurality of pieces of partial data are acquired by performing a tomography scan as the X-ray generating unit 106 rotates around an object 1100. In detail, while the X-ray generating unit 106 moves along a trajectory 1115 around the object 1100, a plurality of pieces of data that are raw data are respectively acquired during a plurality of first through third angular sections 1120, 1130, 1140, and 1150. In this case, the trajectory 1115 may be a circular trajectory used in axial reconstruction described with reference to FIG. 5A or a helical trajectory used in helical reconstruction described with reference to FIG. 5B.

In detail, first partial data corresponding to the first angular section a1 1120 is acquired as the X-ray generating unit 106 emits X-rays toward the object 1100 while rotating around the first angular section a1 1120. Second partial data corresponding to the second angular section a2 1130 is also acquired as the X-ray generating unit 106 emits X-rays toward the object 1100 while rotating around the second angular section a2 1130. Also, third partial data corresponding to the third angular section a3 1140 is acquired as the X-ray generating unit 106 emits X-rays toward the object 1100 while rotating around the third angular section a3 1140. Furthermore, fourth partial data corresponding to the fourth angular section a4 1150 is acquired as the X-ray generating unit 106 emits X-rays toward the object 1100 while rotating around the fourth angular section a4 1150.

An operation of generating first information based on a plurality of pieces of partial data will now be described in more detail with reference to FIGS. 12 through 15.

Figure 12A:
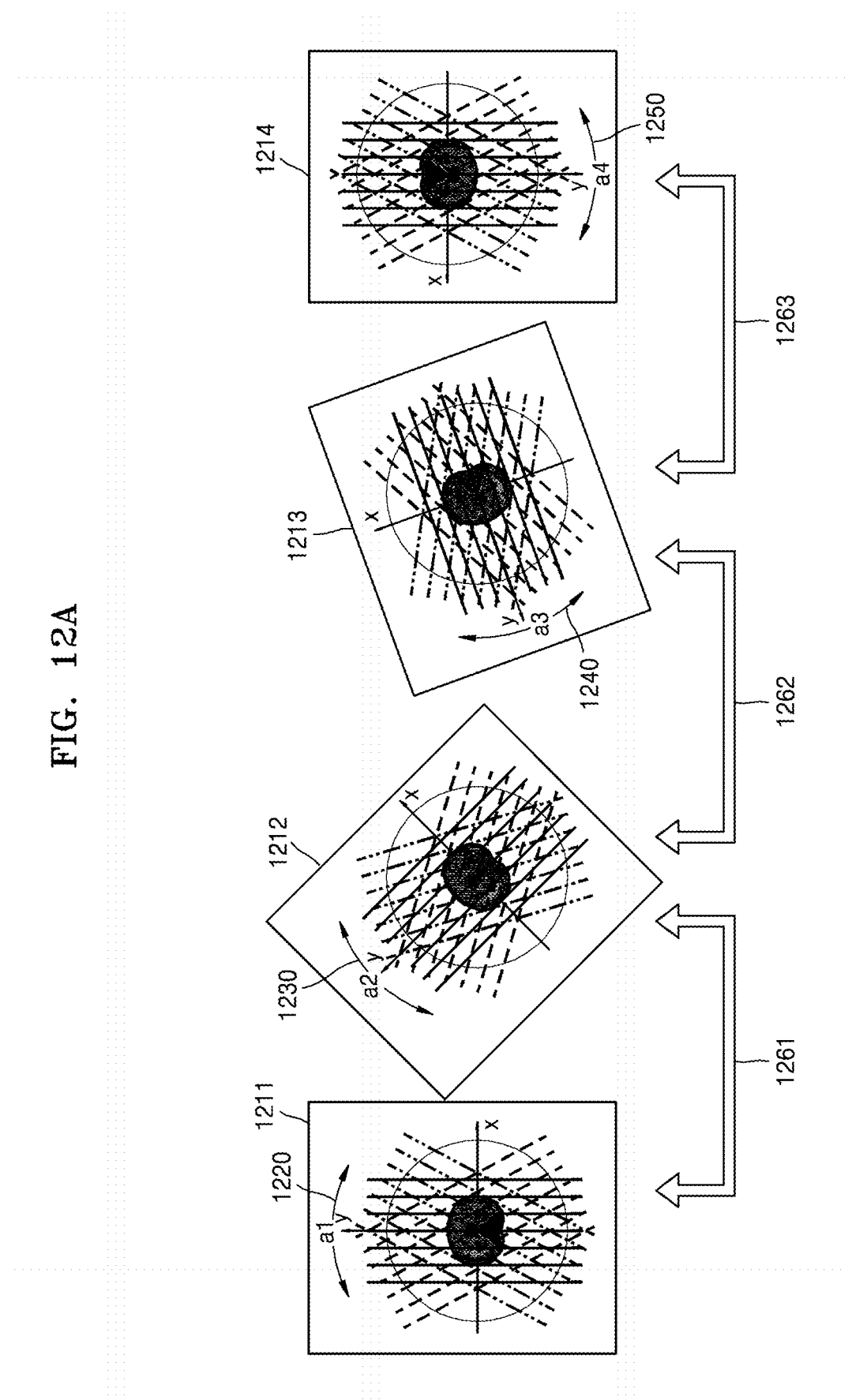
FIG. 12A is another diagram for explaining measurement of motion of an object.

FIG. 12A is another diagram for explaining measurement of motion of an object.

The image processing unit 820 may compare two pieces of partial data respectively corresponding to two adjacent angular sections among a plurality of pieces of partial data and acquire first information based on a comparison result.

A first angular section a1 1220, a second angular section a2 1230, a third angular section a3 1240, and a fourth angular section a4 1250 shown in FIG. 12A respectively correspond to the first angular section a1 1120, the second angular section a2 1130, the third angular section a3 1140, and the fourth angular section a4 1150 described with reference to FIG. 11.

Referring to FIG. 12A, the image processing unit 820 may compare two pieces of partial data respectively corresponding to two adjacent angular sections among a plurality of pieces of partial data, e.g., first and second partial data acquired respectively during the first and second angular sections 1220 and 1230 (operation 1261), and acquire first information based on a comparison result. In detail, the first information may be acquired by sequentially comparing two pieces of partial data respectively corresponding to two adjacent angular sections among the plurality of pieces of partial data. In other words, the first information may be acquired based on results obtained by respectively comparing the first with second partial data, the second with third partial data, and the third with fourth partial data.

In this case, 'partial data' may be raw data such as at least one projection data or a sinogram. Alternatively, the partial data may be a partial tomography image generated by performing FBP on projection data or a sinogram. Furthermore, the partial data may be a partial tomography image generated by performing backprojection on projection data or a sinogram. The partial data and a partial tomography image will now be described in more detail with reference to FIG. 12B.

FIG. 14 is a diagram for explaining first information representing motion of an object.

FIG. 12B is diagram for explaining partial data and a partial tomography image. In FIG. 12B, the same reference numerals as shown in FIG. 12A represent the same elements.

Referring to FIG. 12B, the image processing unit 820 may acquire a first partial tomography image 1272 based on raw data acquired during a first angular section 1220. In this case, a tomography image may be reconstructed from raw data using various reconstruction methods. Examples of methods of reconstructing a tomography image may include backprojection, FBP, an iterative method, etc.

Backprojection is a technique for reconstructing an image by adding up projection data acquired from a plurality of views back across an image plane. In detail, the backprojection method allows acquisition of an image similar to the real image by using projection data acquired from a plurality of views. Furthermore, filtering may be performed additionally to remove artifacts in a reconstructed image and improve quality of the reconstructed image.

FBP is a technique that improves the performance of backprojection in order to eliminate artifacts or blurring that may occur during backprojection. In a FBP method, raw data is filtered and then backprojected to reconstruct a tomography image.

The FBP method is the most commonly used in reconstruction of a tomography image. This method is easy to implement and is effective in terms of the amount of computation required for image reconstruction. The FBP method is a method of mathematically deriving inverse transform from Radon transform that is a process of acquiring a sinogram from a 2D image. In detail, according to the FBP method, projection data is filtered using a Shepp and Logan filter that is one type of high-pass filters and back-projected to reconstruct an image.

An example where a tomography image is reconstructed using a FBP method will now be described.

First partial data may be a plurality of pieces of projection data respectively acquired from a plurality of views included in the first angular section 1220. Similarly, second partial data may be a plurality of pieces of projection data respectively acquired from a plurality of views included in a second angular section 1230. In this case, the first and second angular sections 1220 and 1230 each have a value less than 180°.

Referring to FIG. 12B, the data acquisition unit 810 acquires the first partial data corresponding to the first angular section 1220. The image processing unit 820 acquires an image 1271 by performing FBP on the first partial data. To make surfaces 1275 and 1276 more clearly visible in the image 1271, filtering may be performed on the image 1271 to obtain the first partial tomography image 1272 which is finally reconstructed from the first partial data. In detail, the first partial tomography image 1272 may be an incomplete image reconstructed using a PAR method. On the first partial tomography image 1272, a portion of a surface that forms the object 1201 is shown.

Furthermore, the data acquisition unit 810 acquires the second partial data corresponding to the second angular section 1230. The image processing unit 820 acquires an image 1281 by performing FBP on the second partial data. To make surfaces 1285 and 1286 more clearly visible in the image 1281, filtering may be performed on the image 1281 to obtain a finally reconstructed second partial tomography image 1282. In detail, the second partial tomography image 1282 may be an incomplete image reconstructed using a PAR method. On the second partial tomography image 1282, a portion of a surface that forms the object 1201 is shown.

The image processing unit 820 may compare two partial images respectively corresponding to two adjacent angular sections and reconstructed using a PAR method and acquire first information based on a comparison result.

In detail, the image processing unit 820 may compare the first and second partial tomography images 1272 and 1282 respectively corresponding to the first and second angular sections 1220 and 1230 and acquire first information based on a comparison result.

Figure 13:
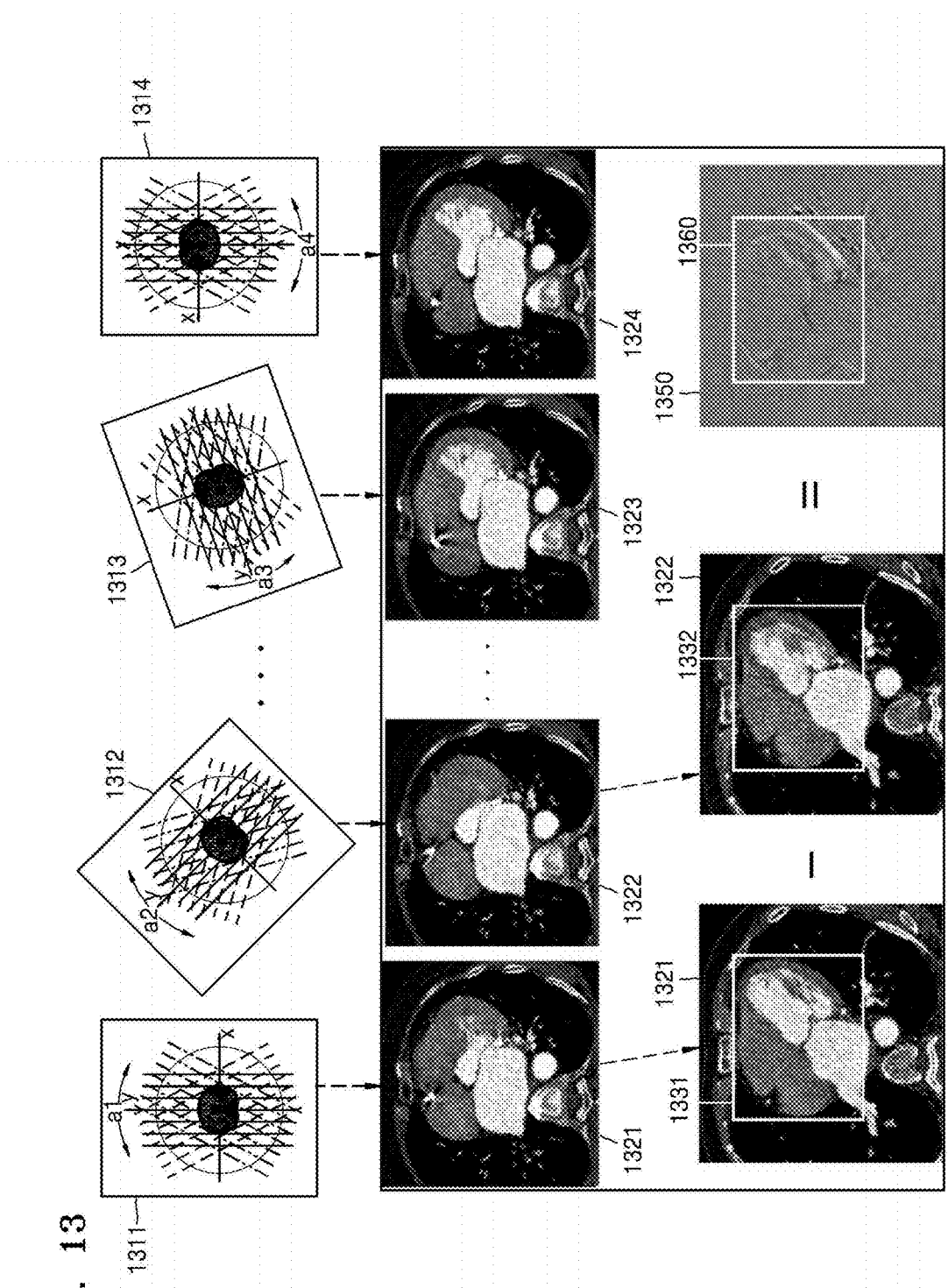
FIG. 13 is another diagram for explaining measurement of motion of an object.

FIG. 13 is another diagram for explaining measurement of motion of an object.

A first angular section a1 1311, a second angular section a2 1312, a third angular section a3 1313, and a fourth angular section a4 1314 shown in FIG. 13 respectively correspond to the first angular section a1 1220, the second angular section a2 1230, the third angular section a3 1240, and the fourth angular section a4 1250 described with reference to FIG. 12A. Furthermore, first and second partial tomography images 1321 and 1322 respectively correspond to the first and second partial tomography images 1272 and 1282 shown in FIG. 12B.

For convenience of explanation, FIG. 13 illustrates an example where the first and second partial tomography images 1321 and 1322 are complete images.

The image processing unit 820 acquires a plurality of first through fourth partial tomography images 1321 through 1324 respectively corresponding to a plurality of angular sections 1311 through 1314. The image processing unit 820 may also acquire first information by repeatedly comparing two adjacent ones of the plurality of first through fourth partial tomography images 1321 through 1324.

An operation of comparing the first and second partial tomography images 1321 and 1322 in order to acquire the first information will now be described by way of an example.

Figure 14A:
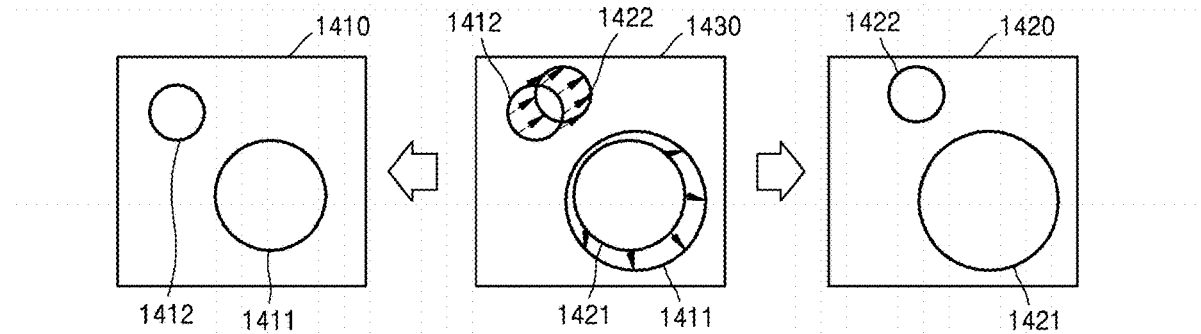
FIGS. 14A through 14C are diagrams for explaining first information representing motion of an object.
Figure 14B:
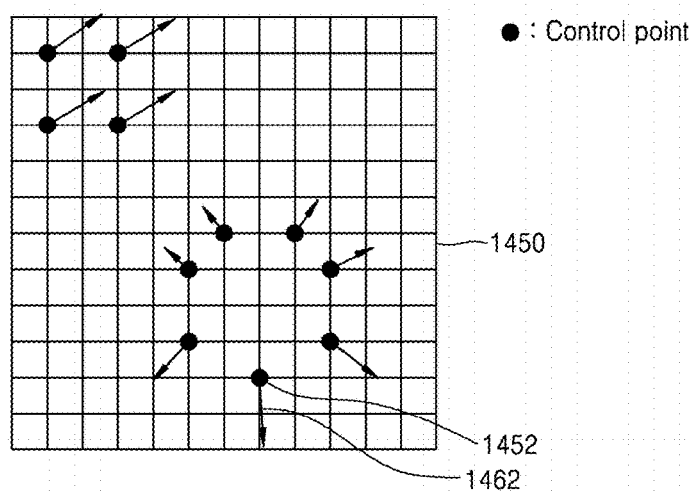
Figure 14C:
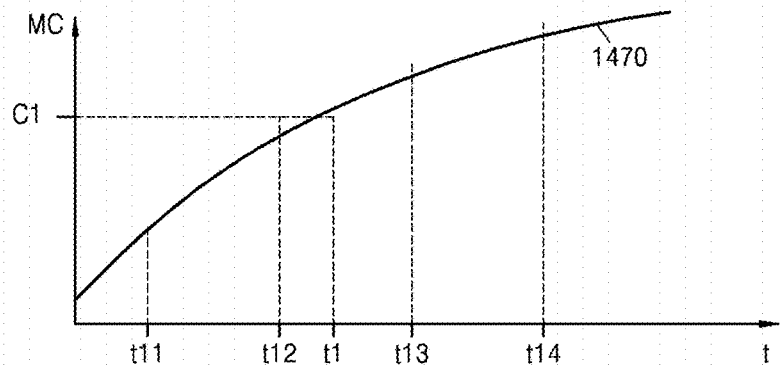

FIGS. 14A through 14C are diagrams for explaining first information representing motion of an object. First and second partial tomography images 1410 and 1420 shown in FIG. 14A respectively correspond to the first and second partial tomography images 1321 and 1322 shown in FIG. 13. For convenience of explanation, the first and second partial tomography images 1410 and 1420 are illustrated in a simplified form. Furthermore, it is assumed hereinafter that the first and second partial tomography images 1410 and 1420 are 2D images, and a surface of the object is depicted as an edge in an image.

Referring to FIG. 14A, the first and second partial tomography images 1410 and 1420 are schematic representations of tomography images obtained by scanning a moving object. Furthermore, at least one surface 1411 and 1412 (or 1421 and 1422) included in the object is represented by a circular entity as shown in FIG. 14A.

In detail, to acquire the first information indicating motion of the object, the image processing unit 820 respectively compares the surfaces 1411 and 1412 in the first partial tomography image 1410 with their corresponding surfaces 1421 and 1422 in the second partial tomography image 1420. Then, the image processing unit 820 may calculate the amount of motion of the object based on comparison results as shown in a comparison image 1430.

FIG. 14A illustrates an example where 2D tomography images, e. g., the first and second partial tomography images 1410 and 1420 are reconstructed using a PAR method. Entities represented as surfaces in a 3D tomography image may be depicted as edges (e.g., 1411 and 1412 or 1421 and 1422) in a 2D tomography image (e.g., the first or second partial tomography image 1410 or 1420) as shown in FIG. 14A.

The image processing unit 820 may determine the extent of motion of an object by comparing a difference between its corresponding edges (e. g., comparing the surfaces 1411 and 1412 with 1421 and 1422) respectively included in the first and second partial tomography images 1410 and 1420 and representing the same surface of the object.

Furthermore, the image processing unit 820 may reconstruct first and second partial tomography images as 3D tomography images and use the same for determining the amount of motion of the object. If the first and second partial tomography images are reconstructed as 3D tomography images, the image processing unit 820 may determine the amount of motion of the object by comparing a difference between corresponding edges respectively included in the first and second partial tomography images and representing the same surface of the object.

Since the first and second partial tomography images 1410 and 1420 are reconstructed from raw data respectively acquired during two adjacent angular sections, the first and second partial tomography images 1410 and 1420 are obtained by imaging similar regions of the object. In detail, there is an overlapping portion between imaged regions of the object respectively shown in the first and second partial tomography images 1410 and 1420. Thus, by comparing the first and second partial tomography images 1410 and 1420 with each other, the same regions of the object in the first and second partial tomography images 1410 and 1420 may be compared with each other, and thus motion of the object may be detected.

If a tomography scan is performed on the moving object, corresponding regions of the object in the first and second partial tomography images 1410 and 1420 are different from each other in at least one of a size, a position, and a form thereof.

Referring to FIG. 14B, by comparing surfaces representing the same portions of an object in two tomography images, a motion vector representing a difference between positions of the compared surfaces and a direction thereof may be calculated. The motion vector may be used as the amount of motion of the object. In this case, information including motion vectors and representing the amount of motion of a predetermined portion of the object may be a motion vector field (MVF) 1450. In other words, the MVF 1450 represents the amount of motion of a surface forming the object.

In detail, the image processing unit 820 may calculate the MVF 1450 including a motion vector (e.g., 1462) representing a difference in positions of the same point (e.g., 1452) of the object in the two images and a direction of the same point 1452.

In this case, the MVF 1450 may be information acquired for measuring the amount of motion of the object, and the amount of motion of the object may be measured using non-rigid registration. The amount of motion of the object may be measured using various other motion measurement techniques such as rigid registration, optical flow, feature matching, etc.

In detail, the image processing unit 820 may mask a portion of the object in a partial tomography image, whose motion is to be measured, and extract motion information from the masked portion of the object.

The image processing unit 820 may mask at least one body part of an object in each of a plurality of partial tomography images and measure motion of an edge included in the masked at least one body part as the global motion. For example, the image processing unit 820 may mask a body part having a bone region including at least one of ribs and vertebra in each of a plurality of partial tomography images, compare the masked bone regions in two adjacent partial tomography images (e.g., 1410 and 1420) with each other, and measure the global motion.

Alternatively, the image processing unit 820 may mask a predetermined organ included in the object, e.g., a lung region, compare the masked lung regions in two adjacent partial tomography images (e. g., 1410 and 1420) with each other, and measure motion of the first region.

Furthermore, the image processing unit 820 may measure the global motion by using rigid registration. The rigid registration is an algorithm for matching motion such as rotation and translation of the object.

For example, the image processing unit 820 may set at least one landmark included in a bone included in the object in each of the first and second partial tomography images 1410 and 1420 and transform at least one of the first and second partial tomography images 1410 and 1420 so as to minimize a distance between the first and second partial tomography images 1410 and 1420. In detail, the image processing unit 820 obtains a rotation and translation matrix that minimizes the distance between corresponding landmarks respectively set in the first and second partial tomography images 1410 and 1420 and registers the first and second partial tomography images 1410 and 1420 together by using the obtained rotation and translation matrix. In this case, the amount of motion made based on the rotation and translation matrix may be the amount of motion of the object between the first and second partial tomography images 1410 and 1420.

As another example, the image processing unit 820 may obtain a rotation and translation matrix based on a pixel intensity similarity between landmarks respectively set in the first and second partial tomography images 1410 and 1420 and register the first and second partial tomography images 1410 and 1420 together by using the obtained rotation and translation matrix. In this case, the pixel intensity similarity may be a sum of square differences (SSD) value. As another example, the pixel intensity similarity may be a sum of absolute differences (SAD) value, a mean of absolute differences (MAD) value, a signal to noise ratio (SNR) value, a mean square error (MSE) value, a peak signal to noise ratio (PSNR) value, or a root mean square error (RMSE) value.

On the other hand, non-rigid registration is an algorithm for matching states between non-rigid objects. The image processing unit 820 may measure motion of the first region by using non-rigid registration.

For example, the image processing unit 820 may perform non-rigid registration between the first and second partial tomography images 1410 and 1420 by using a pixel or voxel based demons algorithm.

In detail, the image processing unit 820 may set a plurality of control points in an image grid representing an image. The image processing unit 820 sets a plurality of control points in each of the first and second partial tomography images 1410 and 1420 and computes an optimal motion vector between corresponding set two control points. In this case, the corresponding two control points respectively set in the first and second partial tomography images 1410 and 1420 may be extracted based on intensity similarity.

Referring to FIG. 14B, the image processing unit 820 may acquire the MVF 1450 describing a difference between the first and second partial tomography images 1410 and 1420 on a 3D image grid corresponding to the first and second partial tomography images 1410 and 1420. Based on the acquired MVF 1450, image processing unit 820 may register the first and second partial tomography images 1410 and 1420 together by warping at least one of the first and second partial tomography images 1410 and 1420.

Furthermore, the image processing unit 820 may perform image registration by using a kernel-based method such as B-spline or thin-plate splines. According to the kernel-based method, landmarks are set and image registration is performed using an intensity similarity between the set landmarks.

As described above, the image processing unit 820 may measure the amount of the global motion by performing rigid registration between the first and second partial tomography images 1410 and 1420 and the amount of motion of the first region by performing non-rigid registration therebetween.

Furthermore, the image processing unit 820 acquires first information representing motion of the object by reflecting the global motion of the object in the motion of the first region. In detail, if the object rotates or translates while lungs included in the first region continue to move due to a respiratory motion, motion due to rotation or translation of the object itself may occur in the lungs as well, in addition to the respiratory motion. In other words, if the object translates from the left side to the right side as the lungs expands due to the respiratory motion, the lungs may also translate from the left side to the right side while expanding at the same time. Thus, the image processing unit 820 acquires the first information representing motion of the object by reflecting the global motion of the object in the motion of the first region.

FIG. 14C is a graphical representation of first information indicating motion of the object. In a graph 1470, y-axis and x-axis denote the amount of motion and time, respectively. In detail, the first information represents motion of the object during a time corresponding to the entire interval including a plurality of consecutive angular sections. The first information may be acquired during the entire time interval including time points t11 through t14 that respectively correspond to the first partial tomography image 1410, the second partial tomography image 1420, a third partial tomography image (e.g., the third partial data acquired during the third angular section a3 1240 shown in FIG. 12A) and a fourth partial tomography image (e. g., the fourth partial data acquired during the fourth angular section a4 1250 shown in FIG. 12A).

The image processing unit 820 acquires the first information representing motion of the object during an angular section between the time points t11 and t12 by comparing the first and second partial tomography images 1410 and 1420 with each other. The image processing unit 820 also acquires the first information representing motion of the object during an angular section between the time points t12 and t13 by comparing the second partial tomography image 1420 with the third partial tomography image. Furthermore, the image processing unit 820 acquires the first information representing motion of the object during an angular section between the time points t13 and t14 by comparing the third and fourth partial tomography images with each other.

As described above, the image processing unit 820 may acquire the first information representing motion of the object during the entire time interval by repeatedly comparing two partial tomography images respectively acquired during two adjacent angular sections.

Furthermore, the first information may be created by a MVF as described with reference to FIG. 14B. The first information may also be created by the graph 1470 representing the magnitude of a vector included in the MVF, as described with reference to FIG. 14C. Alternatively, the first information may be represented by a function expression describing the amount of motion over time.

Figure 15A:
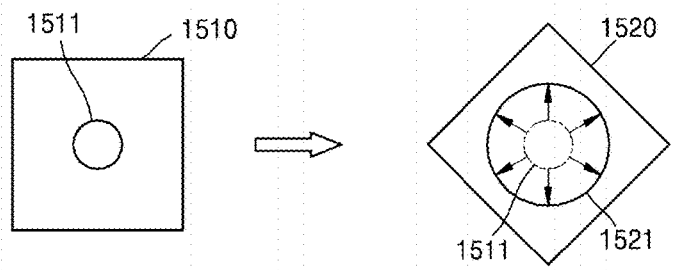
FIGS. 15A and 15B are other diagrams for explaining first information representing motion of an object.
Figure 15B:
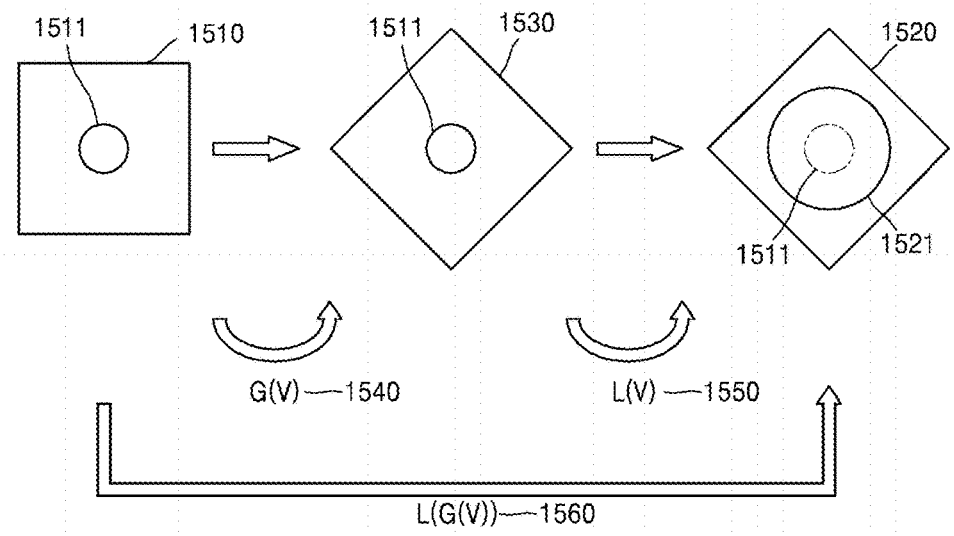

FIGS. 15A and 15B are other diagrams for explaining first information representing motion of an object.

FIG. 15A is a schematic diagram illustrating motion of an object 1510 that rotates in a clockwise direction while an organ 1511 included in a first region of the object expands. In FIGS. 15A and 15B, the organ 1511 and the object 1510 may respectively correspond to a lung 1511 and an abdominal cross-section. In other words, FIGS. 15A and 15B are schematic diagrams illustrating motion of the abdomen that is the object 1510 if a patient breathes while turning his or her body right at the same time.

Referring to FIG. 15A, the lung 1511 expands due to respiratory motion to be imaged like a lung 1521, and the object 1510 moves like an object 1520 as the patient rotates.

Referring to FIG. 15B, motion of the object 1510 described with reference to FIG. 15A may be divided into the global motion caused by the patient's turning his body right and motion of the first region caused by expansion of the lung.

In FIG. 15B, if the object 1510 rotates to be in the same state as an object 1530, rotational motion of the object 1510 that is the global motion of the object 1510 may be represented by a function G(V) 1540. Motion of the first region like the lung 1521 due to expansion of the lung 1511 may be represented by a function L(V) 1550. Furthermore, the motion of the object obtained by reflecting the global motion in the motion of the first region may be represented by a function L(G(V)) 1560 by substituting the function G(V) 1540 into the function L(V) 1550.

In other words, as described above, the image processing unit 820 may acquire the first information representing motion of an object in the form of a function.

Figure 16:
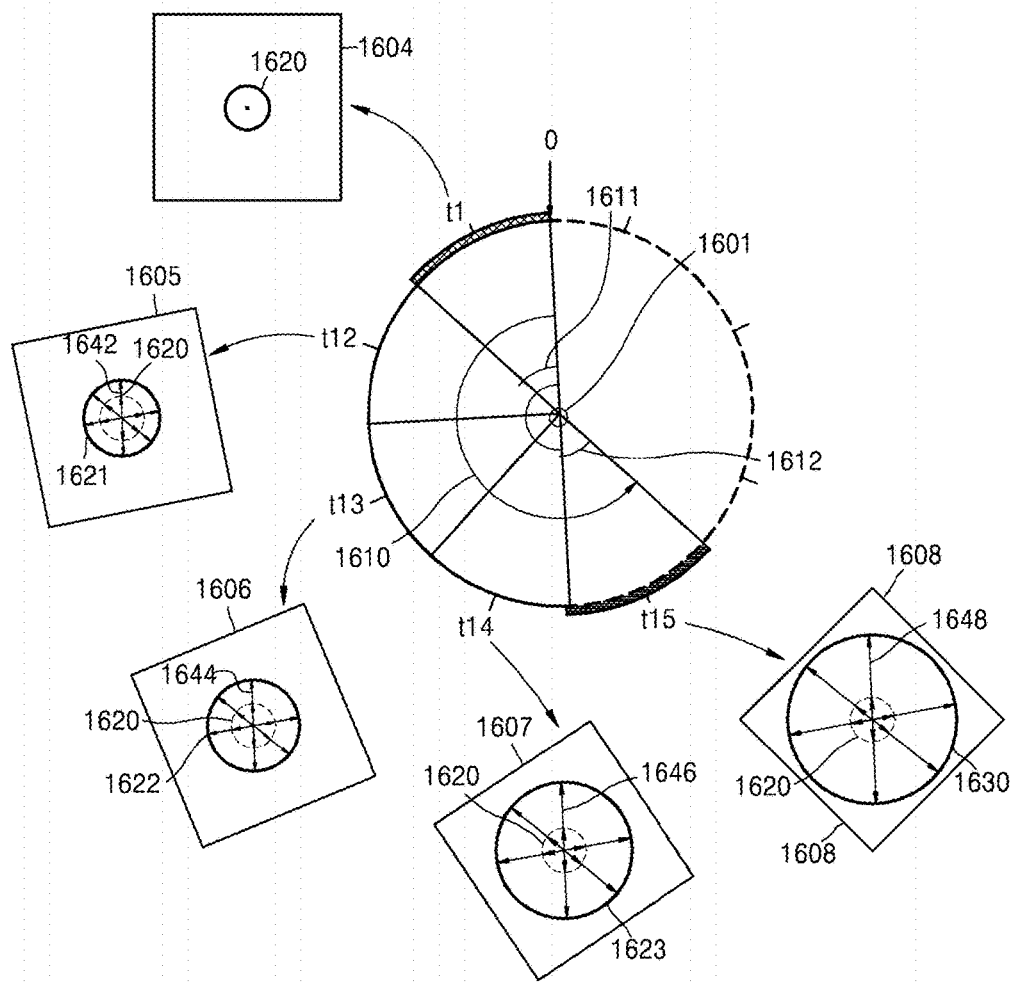
FIG. 16 illustrates a change in a state of an object with respect to time.

FIG. 16 illustrates a change in a state of an object 1601 with respect to time.

Referring to FIG. 16, time points t11 through t14 may respectively correspond to the time points t11 through t14 shown in FIG. 14C.

Since first information represents the amount of motion of an object over time, a state of the object may be predicted based on the first information. For example, as apparent from the graph 1470 of FIG. 14C, a value along the y-axis that is the amount of motion made during an interval between the time points t11 and 14 gradually increases, which means that the amount of motion of the object has increased. It may also be predicted that the object has gradually expanded during an interval between the time points t11 through t14.

FIG. 16 illustrates an example where the object 1601 moves like the object 1510 described with reference to FIG. 15. In other words, FIG. 16 is a schematic diagram illustrating motion of an object 1604 that rotates right during expansion of a lung that is an organ included in a first region of the object 1604.

Referring to FIG. 16, based on the first information, the image processing unit 820 may predict that a lung of an object 1604 in a first partial tomography image corresponding to a time point t11 has a first size 1620, and that a lung of an object 1605 in a second partial tomography image corresponding to a time point t12 has a second size 1621.

Furthermore, in the same manner, the image processing unit 820 may predict a state of the object 1601 at a predetermined point included in the entire time interval corresponding to a plurality of angular sections 1610, based on the first information.

In other words, the image processing unit 820 may predict states of the object 1601 and the first region based on the first information and perform motion correction based on the predicted states. In detail, the image processing unit 820 may warp a tomography image to fit a state of an object at a specific time point, which is predicted based on the first information, thereby reconstructing a final tomography image showing a state of the object at the specific time point accurately. In this case, warping means adjusting the size of an object in an image according to a predicted size by translating, rotating, expanding, and/or contracting the object. In other words, the image processing unit 820 may reconstruct a final tomography image by performing motion correction on an initial tomography image reconstructed from raw data.

Thus, the image processing unit 820 may reconstruct a final tomography image that reflects an object at a specific point with a high degree of accuracy.

For example, the image processing unit 820 may reconstruct a final tomography image by performing motion correction on a portion included in a first region of an object that is an ROI selected by the user for diagnosis. Referring back to FIG. 14C, the amount of motion of an object at a first time point t1 in the entire time interval has a value C1. In this case, the image processing unit 820 may reconstruct a final tomography image by warping an object in a tomography image to be in a state corresponding to the amount of motion C1.

As another example, the image processing unit 820 may reconstruct a final tomography image by primarily correcting global motion of the object in a tomography image showing the object based on the first information and secondarily correcting motion of the first region in the primarily corrected tomography image.

Figure 17A:
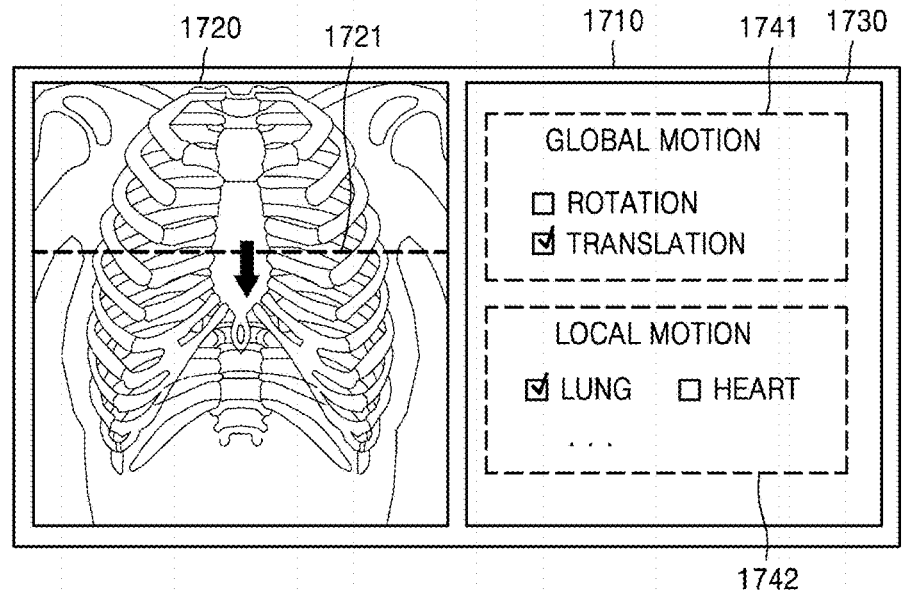
FIGS. 17A and 17B illustrate user interface screens output from a tomography imaging apparatus, according to an exemplary embodiment.
Figure 17B:
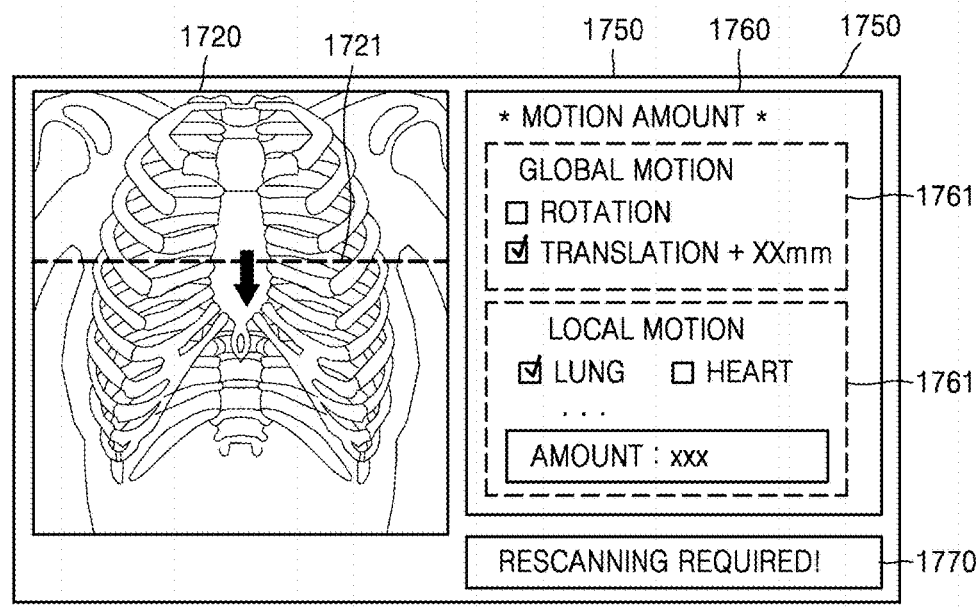

FIGS. 17A and 17B respectively illustrate user interface screens 1710 and 1750 output from a tomography imaging apparatus, according to an exemplary embodiment;

The image processing unit 820 may generate second information including information about motion of an object, based on first information. In this case, the second information may include at least one piece of information obtained by quantifying the amount of motion of the object, information obtained by classifying the amount of motion of the object into a plurality of stages and indicating the amount of motion of the object by each of the plurality of stages, numerical information indicating the amount of motion of the object, and information indicating the type of motion of the object.

In detail, the second information is obtained by classifying the amount of motion of the object into a plurality of stages according to the magnitude thereof and indicating the amount of motion for each of the plurality of stages. For example, the second information may be information obtained by classifying the amount of motion of the object into a plurality of stages, e.g., three stages including 'stage 1—occurrence of little motion', 'stage 2—occurrence of motion of an allowable amount due to application of motion correction based on the first information', and stage 3—occurrence of motion whose amount exceeds a predetermined threshold' and indicating the amount of motion for each of the plurality of stages.

Furthermore, the information obtained by classifying the amount of motion into a plurality of stages and indicating the same for each stage may be indicated separately for each of the global motion and motion of the first region. Furthermore, the information may be indicated for motion of the object corresponding to a sum of the global motion and the motion of the first region.

The numerical information indicating the amount of motion of the object may include information representing the amount of motion of a real object as numerical values. For example, if a patient rotates his or her body to the left, information including a specific rotational angle of the patient may be indicated.

Furthermore, the information indicating the type of motion of the object may include at least one of the type of global motion and the type of motion of the first region. In detail, the global motion may include at least one of rotation and translation of the object. The motion of the first region may be classified and indicated by tissue and an organ in the first region.

Referring to FIG. 17A, the user interface screen 1710 may include a tomography image 1720 showing a current slice 1721 undergoing a tomography scan and second information 1730 representing motion of an object including global motion 1741 that occurs in the object being imaged at the current slice 1721 and motion 1742 of a first region.

The type of the global motion 1741 and the type (not shown) of motion of an organ (e.g., a lung) to be scanned in the motion 1742 of the first region may be indicated by the second information 1730.

Referring to FIG. 17B, the user interface screen 1750 may include a tomography image 1720 showing a current slice 1721 undergoing a tomography scan and second information 1760 representing motion of an object including global motion 1761 that occurs in the object being imaged at the current slice 1721 and motion 1765 of a first region. As shown in FIG. 17B, the second information 1760 may include specific numerical values.

Furthermore, the image processing unit 820 may quantify motion of an object into a plurality of stages according to the amount of the motion of the object and output an alarm message 1770 corresponding to each of the plurality of stages. For example, if it is determined based on the amount of motion of the object that tomography rescanning is required, the image processing unit 820 may control the alarm message 1770 to be output.

Figure 18A:
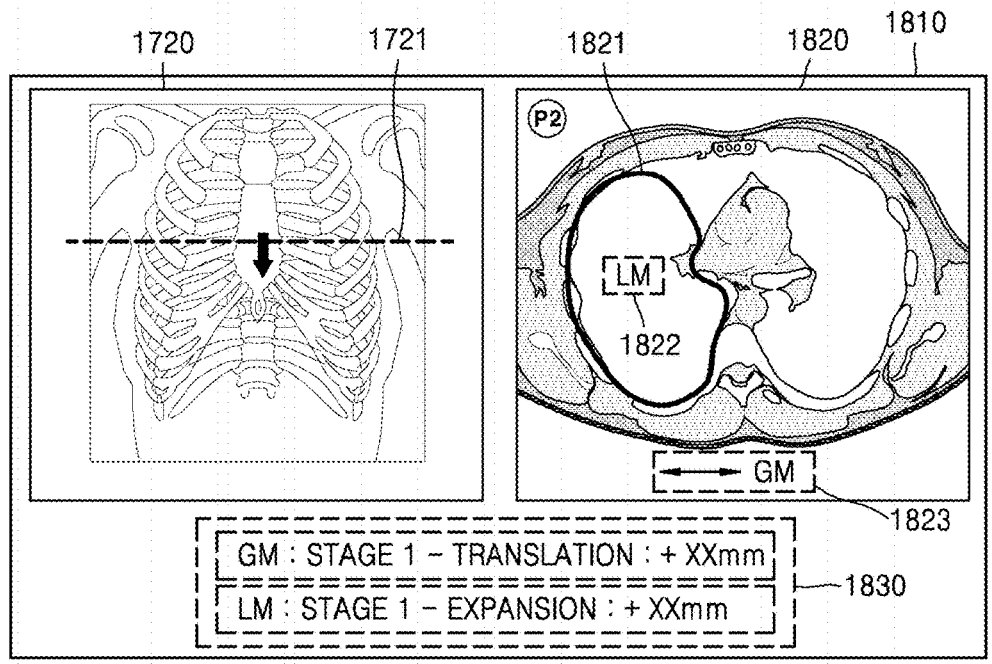
FIGS. 18A and 18B illustrate user interface screens output from a tomography imaging apparatus, according to another exemplary embodiment.
Figure 18B:
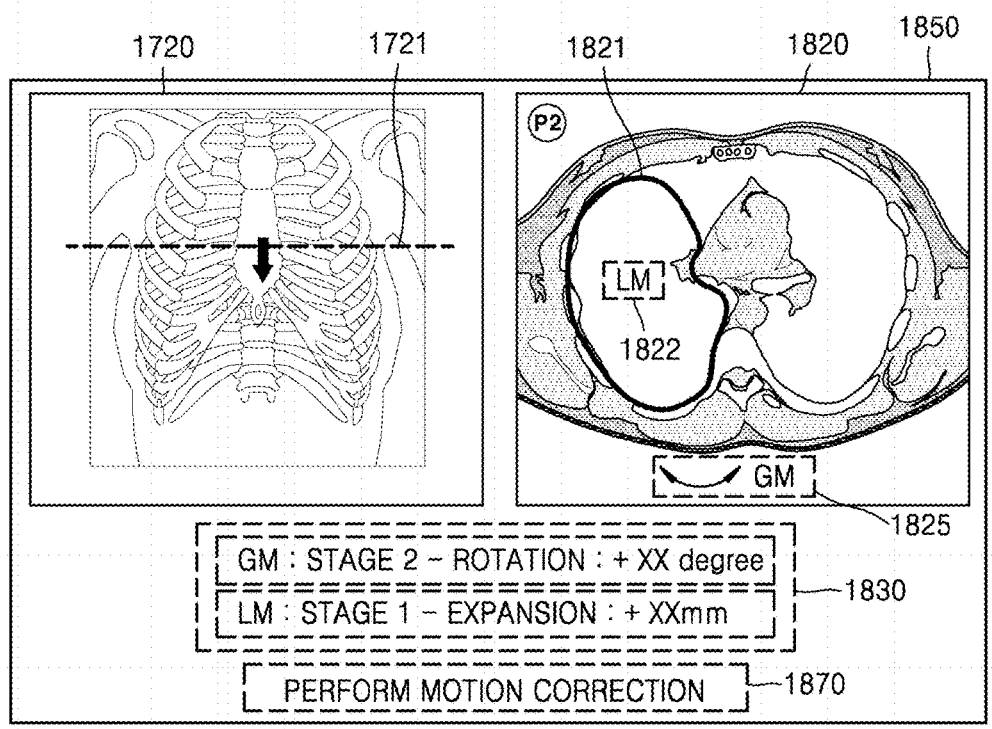

FIGS. 18A and 18B illustrate user interface screens 1810 and 1850 output from a tomography imaging apparatus, according to another exemplary embodiment.

Referring to FIG. 18A, the user interface screen 1810 may further include a tomography image 1820 reconstructed at a current slice 1721. The reconstructed tomography image 1820 may be a final tomography image that has undergone motion correction based on first information.

Furthermore, markers 1822 and 1823 respectively indicating global motion and motion of a first region 1821 may be indicated on the reconstructed tomography image 1820.

Furthermore, the user interface screen 1810 may further include second information 1830 obtained by quantifying motion of an object.

The second information may include information indicating whether rescanning is required based on the amount of motion of the object. In detail, the user may set the amount of motion determined as requiring rescanning to a threshold value via the user interface unit 850. Furthermore, the image processing unit 820 may set a threshold value by defining an allowable range of the amount of motion. If the measured amount of motion of the object exceeds the threshold value based on the first information, the image processing unit 820 may output an alarm signal notifying that rescanning is required. In detail, the alarm signal may be output to the user interface screen 1810 so that the user visually recognizes the alarm signal. Furthermore, the alarm signal may be output as an audio message via a speaker (not shown) so that the user may acoustically recognize the alarm signal.

Referring to FIG. 18B, the user interface screen 1850 may include the reconstructed tomography image 1820, the second information 1830, and the alarm message 1870.

As described above, by displaying a tomography image before undergoing motion correction, a motion-compensated tomography image, second information indicating motion of the object, and an alarm message, the user may intuitively recognize the extent of motion of the object.

FIGS. 19A and 19B are diagrams for explaining reconstruction of a tomography image using a half reconstruction method. In particular, FIGS. 19A and 19B are diagrams for explaining reconstruction of a target image of a stationary object. In detail, FIG. 19A is a diagram for explaining a tomography scan that is performed as the X-ray generating unit 106 rotates around an object 1901. FIG. 19B is a diagram for explaining an operation of backprojecting pieces of projection data acquired by filtering raw data obtained from a tomography scan.

FIGS. 19A and 19B illustrate an example where a tomography scan is performed as the X-ray generating unit 106 rotates around the object 1901 and a tomography image is reconstructed using FBP. As shown in FIGS. 19A and 19B, the object 1901 includes one circular entity 1902. Furthermore, although one period of angular sections needed to reconstruct a tomography image according to a half reconstruction method is 180° plus fan angle, for convenience of explanation, FIGS. 19A and 19B illustrate an example where one tomography image is reconstructed from raw data acquired by performing a tomography scan as the X-ray generating unit 106 rotates by 180°.

Referring to FIG. 19A, projection data is acquired as the X-ray generating unit 106 emits X-rays toward the object 1901 at each of a plurality of points having a predetermined angular section as it moves along a circular source trajectory 1910. Then, filtered projection data is acquired by performing filtering on the projection data. In FIG. 19A, the plurality of points along the circular source trajectory 1910 represent points where the X-ray generating unit 106 is located to emit X-rays. For example, the X-ray generating unit 106 may emit X-rays toward the object 1901 by moving at predetermined intervals such as every 0.5-degree, 1-degree, or 3-degree intervals. The X-ray generating unit 106 rotates from a time point t11 to a time point t15. Thus, the time points t11 and t15 respectively correspond to rotational angles of 0° and 180°.

Furthermore, pieces of projection data acquired as the X-ray generating unit 106 rotates from the time point t11 to the time point t15 may correspond to raw data 1913, 1914, 1915, 1916, and 1917 needed to reconstruct a tomography image as described with reference to FIGS. 18A and 18B.

In detail, when the X-ray generating unit 106 emits an X-ray toward the object 1901 at the time point t11, the X-ray emitted in a direction 1932 passes through an object 1901 to acquire a signal 1931. The acquired signal 1931 may have varying values on a surface of the object 1901 due to a difference in the rate of penetration of the X-ray through materials. In detail, values of the signal 1931 may vary on a surface that is parallel to the direction 1932.

Furthermore, when the X-ray generating unit 106 emits an X-ray toward the object 1901 at time point t12, the X-ray emitted in a direction 1934 passes through an object 1914 to acquire a signal 1933. The acquired signal 1933 may have varying values on a surface that is parallel to the direction 1934.

Furthermore, when the X-ray generating unit 106 emits an X-ray toward the object 1901 at time point t13, the X-ray emitted in a direction 1936 passes through an object 1915 to acquire a signal 1935. The acquired signal 1935 may have varying values on a surface that is parallel to the direction 1936.

Furthermore, when the X-ray generating unit 106 emits an X-ray toward the object 1901 at time point t14, the X-ray emitted in a direction 1938 passes through an object 1916 to acquire a signal 1937. The acquired signal 1937 may have varying values on a surface that is parallel to the direction 1938.

Furthermore, when the X-ray generating unit 106 emits an X-ray toward the object 1901 at time point t15, the X-ray emitted in a direction 1924 passes through an object 1917 to acquire a signal 1939. The acquired signal 1939 may have varying values on a surface that is parallel to the direction 1924.

Furthermore, since the signal 1931 includes information about the surface that is parallel to the direction 1932, an image 1951 acquired by performing FBP of the signal 1931 contributes to imaging the surface disposed in the direction 1932. Similarly, since the signal 1933 includes information about the surface disposed in the direction 1934, filtered projection data corresponding to the signal 1933 contributes to imaging the surface disposed in the direction 1934. That is, projection data acquired at each view contributes to imaging a surface of the object corresponding to the view. This method may be explained using a Fourier slice theorem that describes the relationship between a value of projection data acquired by projecting a parallel beam to the object 1901 and a frequency component. In this case, a 'view' corresponds to a direction, a position, and/or a rotational angle where the X-ray generating unit 106 emits an X-ray toward the object 1901.

Furthermore, the DAS 116 described with reference to FIG. 2 may acquire a signal (e.g., the signal 1931). The image processing unit 126 may process the acquired signal 1931 to generate filtered projection data and then backprojects the filtered projection data to form the image 1951.

In detail, when a plurality of pieces of filtered projection data are acquired while the X-ray generating unit 106 emits X-rays at a plurality of points (a plurality of views) during rotation thereof, the plurality of pieces of filtered projection data are accumulated and backprojected to reconstruct a tomography image. In other words, an image representing an object may be obtained by a backprojection process whereby pieces of filtered projection data are applied to image pixels.

Referring to FIG. 19B, a surface of the entity 1902 included in the object 1901 at the time point t11 appears in the back-projected image 1951 corresponding to the time point t11. Then, filtered projection data for a plurality of views, which are acquired during counter-clockwise rotation, are accumulated and backprojected.

For example, pieces of filtered projection data acquired during an angular section of 22.5° are accumulated and backprojected to obtain a backprojected image 1953. The backprojected image 1953 shows a partial surface 1954 of the entity 1902 in the object 1901.

Then, pieces of filtered projection data acquired during an angular section of 45° are accumulated and backprojected to obtain a backprojected image 1955. The backprojected image 1955 shows a partial surface 1956 of the entity 1902 in the object 1901.

Similarly, pieces of filtered projection data acquired during an angular section of 98° are then accumulated and backprojected to obtain a backprojected image 1957. The backprojected image 1957 shows a partial surface 1958 of the entity 1902 in the object 1901.

Furthermore, pieces of filtered projection data acquired during an angular section of 180° are then accumulated and backprojected to obtain a backprojected image 1959. The backprojected image 1959 shows an entire surface 1964 of the entity 1902 in the object 1901

If an object is stationary, at least one of states of the object, e. g., a size, a position, and a shape of the object at a plurality of time points t11 through t15 included in one period of angular sections is the same.

Thus, when a tomography image is reconstructed by accumulating data acquired by performing FBP of a plurality of pieces of projection data corresponding to a plurality of views included in one period of angular sections, blurring caused by motion artifacts does not occur in the finally reconstructed image 1959 since the object is in the same state at each of the plurality of views.

Figure 20A:
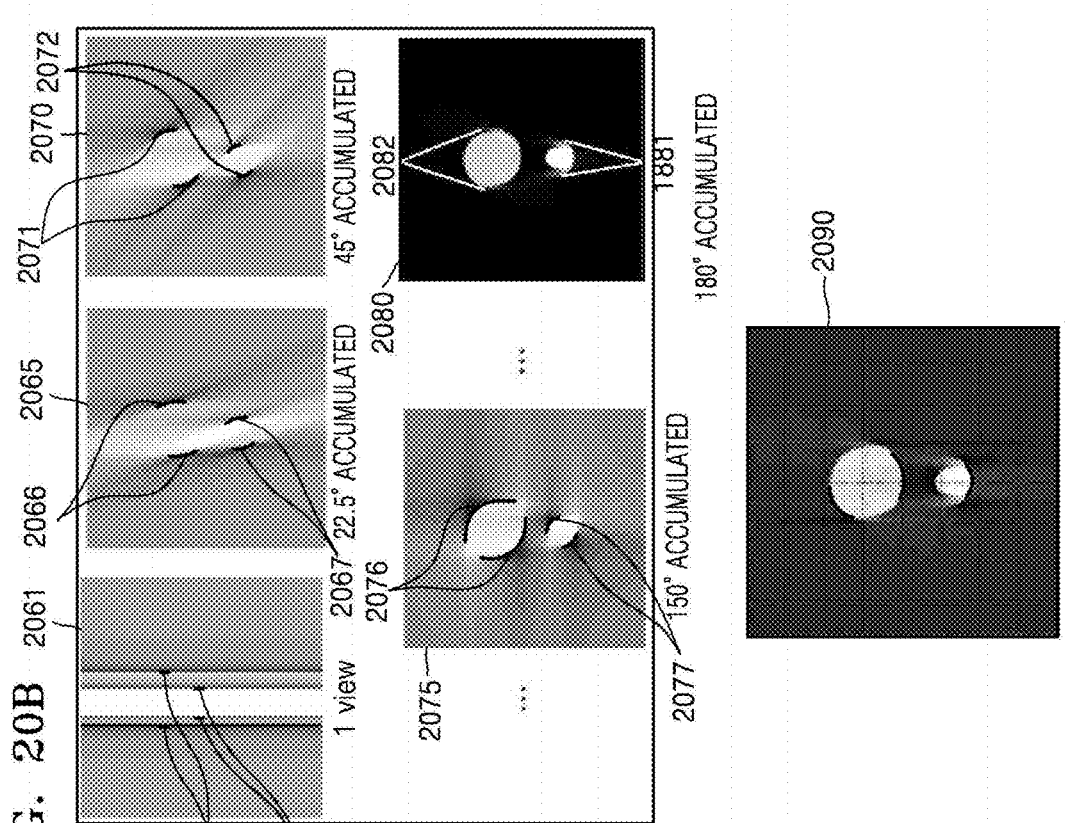
FIGS. 20A and 20B are other diagrams for explaining reconstruction of a tomography image using a half reconstruction method.
Figure 20B:
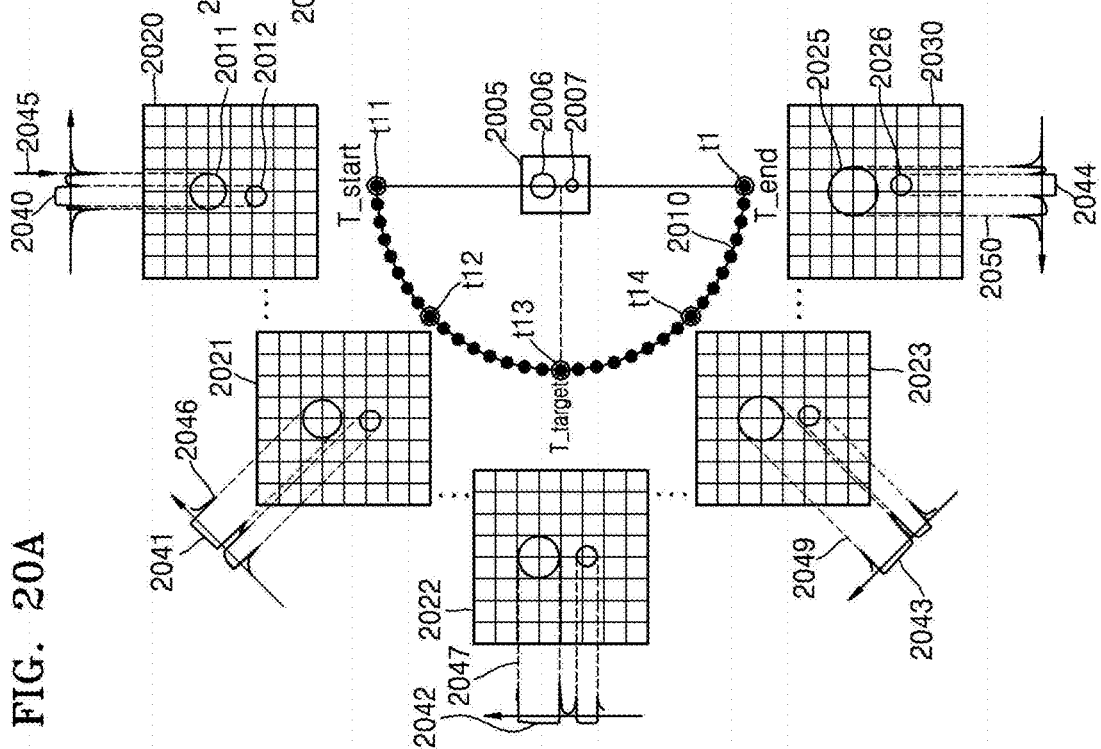

FIGS. 20A and 20B are other diagrams for explaining reconstruction of a tomography image using a half reconstruction method. In detail, FIG. 20A is a diagram for explaining a tomography scan that is performed as the X-ray generating unit 106 rotates around an object 2005. FIG. 20B is a diagram for explaining an operation of backprojecting pieces of projection data acquired by filtering raw data obtained from a tomography scan. In particular, FIG. 20B illustrates an example where a tomography image is reconstructed using FBP. As shown in FIGS. 20A and 20B, the object 2005 includes two circular entities 2006 and 2007. For convenience of explanation, upper and lower circular entities 2006 and 2007 are referred to as first and second entities, respectively. Although one period of angular sections needed to reconstruct a tomography image according to a half reconstruction method is 180° plus the fan angle as described above, for convenience of explanation, FIGS. 20A and 20B illustrate an example where one tomography image is reconstructed from raw data acquired by performing a tomography scan as the X-ray generating unit 106 rotates by 180°.

Referring to FIG. 20A, projection data is acquired as the X-ray generating unit 106 emits an X-ray toward the object 2005 at each of a plurality of points having a predetermined angular section as it moves along a circular source trajectory 2010. Then, filtered projection data is acquired by performing filtering on the projection data. In FIG. 20A, the plurality of points along the circular source trajectory 2010 represent points where X-ray generating unit 106 is located to emit X-rays. For example, the X-ray generating unit 106 may emit X-rays toward the object 2005 by moving at predetermined intervals such as every 0.5-degree, 1-degree, or 3-degree intervals. The X-ray generating unit 106 rotates from a time point t11 to a time point t15. Thus, the time points t11 and t15 respectively correspond to rotational angles of 0° and 180°.

The object 2005 at the time points t11 through t15 may respectively move like objects 2020, 2021, 2022, 2023, and 2030. In detail, the first entity 2006 included in the object 2005 expands in size at its position while the second entity 2007 may move from left to right instead of expanding in size.

In detail, when the X-ray generating unit 106 emits an X-ray toward the object 2005 at the time point t11, the X-ray emitted in a direction 2045 passes through an object 2020 to acquire a signal 2040. The acquired signal 2040 may have varying values on a surface of the object 2020 due to a difference in the rate of penetration of the X-ray through materials. In detail, values of the signal 2040 may vary on a surface that is parallel to the direction 2045.

Furthermore, when the X-ray generating unit 106 emits an X-ray toward the object 2005 at time point t12, the X-ray emitted in a direction 2046 passes through an object 2021 to acquire a signal 2041. The acquired signal 2041 may have varying values on a surface that is parallel to the direction 2046.

Furthermore, when the X-ray generating unit 106 emits an X-ray toward the object 2005 at time point t13, the X-ray emitted in a direction 2047 passes through an object 2022 to acquire a signal 2042. The acquired signal 2042 may have varying values on a surface that is parallel to the direction 2047.

Furthermore, when the X-ray generating unit 106 emits an X-ray toward the object 2005 at time point t14, the X-ray emitted in a direction 2049 passes through an object 2023 to acquire a signal 2043. The acquired signal 2043 may have varying values on a surface that is parallel to the direction 2049.

Furthermore, when the X-ray generating unit 106 emits an X-ray toward the object 2005 at time point t15, the X-ray emitted in a direction 2050 passes through an object 2030 to acquire a signal 2044. The acquired signal 2044 may have varying values on a surface that is parallel to the direction 2050.

Furthermore, since the signal 2040 includes information about the surface disposed in the direction 2045, an image 2061 acquired by performing FBP of the signal 2040 contributes to imaging the surface disposed in the direction 2045. Similarly, since the signal 2041 includes information about the surface disposed in the direction 2046, filtered projection data corresponding to the signal 2041 contributes to imaging the surface disposed in the direction 2046. That is, projection data acquired at each view contributes to imaging a surface of the object corresponding to the view. In this case, a 'view' corresponds to a direction, a position, and/or a rotational angle where the X-ray generating unit 106 emits an X-ray toward the object 2005.

Furthermore, the DAS 116 described with reference to FIG. 2 may acquire a signal (e.g., the signal 2040). The image processing unit 126 may process the acquired signal 2040 to generate filtered projection data and then backprojects the filtered projection data to form the image 2061.

In detail, when a plurality of pieces of filtered projection data are acquired while the X-ray generating unit 106 emits X-rays at a plurality of points (a plurality of views) during rotation thereof, the plurality of pieces of filtered projection data are accumulated and backprojected to reconstruct a tomography image. In other words, an image of an object may be obtained by a backprojection process whereby pieces of filtered projection data are applied to image pixels.

Referring to FIG. 20B, surfaces 2062 and 2063 of the first and second entities 2011 and 2012 included in the object 2020 at the time point t11 appear in the back-projected image 2061 corresponding to the time point t11. Then, filtered projection data for a plurality of views, which are acquired during counter-clockwise rotation, are accumulated and backprojected.

For example, pieces of filtered projection data acquired during an angular section of 22.5° are accumulated and backprojected to obtain a backprojected image 2065. The backprojected image 2065 shows partial surfaces 2066 and 2067 of the first and second entities 2006 and 2007 in the object 2005.

Then, pieces of filtered projection data acquired during an angular section of 45° are accumulated and backprojected to obtain a backprojected image 2070. The backprojected image 2070 shows partial surfaces 2071 and 2072 of the first and second entities 2006 and 2007 in the object 2005.

Similarly, pieces of filtered projection data acquired during an angular section of 150° are then accumulated and backprojected to obtain a backprojected image 2075. The backprojected image 2075 shows partial surfaces 2076 and 2077 of the first and second entities 2006 and 2007 in the object 2005.

Furthermore, pieces of filtered projection data acquired during an angular section of 180° are then accumulated and backprojected to obtain a backprojected image 2080. The backprojected image 2080 shows entire surfaces of the first and second entities 2006 and 2007 in the object 2005.

An image 2090 shown in FIG. 20B is a tomography image of an object, which is finally reconstructed using a backprojection process.

However, a mismatch in surface information between pieces of filtered projection data acquired at each view occurs due to motion of an object. Thus, if a plurality of pieces of filtered projection data acquired during one period of angular sections are accumulated, as shown in FIG. 20B, blurring (2081 and 1882) occurs so surfaces of the first and second entities 2006 and 2007 are unclear.

According to exemplary embodiments, even when an object includes various materials, surfaces, and/or shapes therein, like the object 2005 illustrated in FIGS. 20A and 20B, motion of the object may be estimated and measured accurately without limitation on the type of an object to undergo a tomography scan, and a motion corrected image may be reconstructed based on the estimated motion of the object. Reconstruction of a final tomography image using first information will now be described in more detail with reference to FIGS. 21 through 24.

Figure 21:
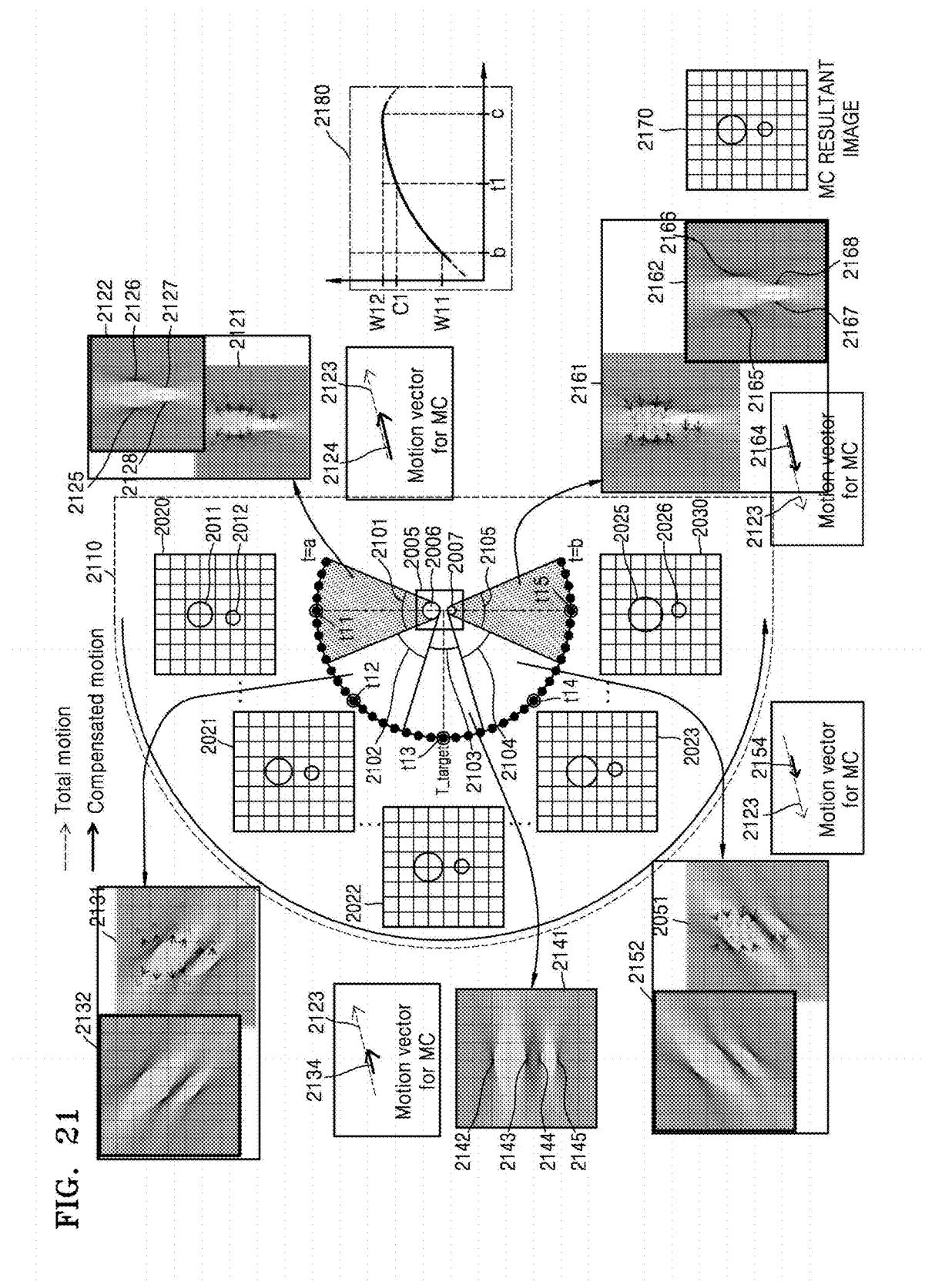
FIG. 21 is a diagram for explaining reconstruction of a motion-corrected final tomography image.

FIG. 21 is a diagram for explaining reconstruction of a motion-corrected final tomography image.

The image processing unit 820 reconstructs an image of an object at a target time point Ttarget based on first information 2180 indicating motion of the object. In this case, the target time point Ttarget is a time point when the image is to be reconstructed, and referring to FIG. 21, time point t13 is the target time point Ttarget for a final tomography image to be reconstructed from raw data. Since the first information 2180 corresponds to the graph 1470 described with reference to FIG. 14C, the same descriptions as those already provided above with respect to FIGS. 14A through 14C are omitted. In the first information 2180, the amount of motion at the time point t13 may have a value of C1.

An operation of generating a final tomography image that is a motion corrected image obtained by performing motion correction on a tomography image based on the first information 2180 will now be described in more detail. FIG. 21 illustrates an example where a final tomography image that is an image representing the object at the time point t13 that is the target time point Ttarget is reconstructed. Furthermore, it is assumed in FIGS. 18 through 21 the time point t13 is a mid time point in one period of angular sections.

As described above with reference to FIGS. 14A through 14C, the first information 2180 may be acquired using the MVF 1450. Referring to FIG. 21, the first information 2180 represents the amount of motion of the object during the entire time interval including one period of angular sections needed for reconstructing a final tomography image. In detail, if the one period of angular sections corresponds to a time interval between time points b and c, the entire time interval in the first information 2180 may include the time interval between the time points b and c.

The extent of motion of the object at the target time point Ttarget may be predicted based on the first information 2180. Alternatively, a state of the object including at least one of a size, shape, and a position of the object at the target time point Ttarget may be predicted using the first information 2180.

As described above with reference to FIGS. 20A and 20B, pieces of projection data acquired at each view or a predetermined angular section included in one period of angular sections contribute to imaging different surfaces or regions of the object.

Before reconstructing a target image, by using the first information, the image processing unit 820 may perform motion correction on a surface or region of the object being imaged using pieces of projection data acquired at time points other than the target time point Ttarget and not on a surface or region of the object being imaged using projection data acquired at the target time point Ttarget.

For convenience of explanation, it is assumed in FIG. 21 that one period of angular sections for pieces of projection data needed for reconstructing a cross-sectional image is divided into first through fifth angular sections 2101 through 2105, and images are obtained by backprojecting pieces of projection data acquired during each of the five angular sections 2101 through 2105. In detail, partial images 2121 and 2131 are obtained by backprojecting pieces of projection data respectively acquired during the first and second angular sections 2101 and 2102. Furthermore, partial images 2141, 2151, and 2161 are obtained by backprojecting pieces of projection data respectively acquired during the third through fifth angular sections 2103 through 2105.

Referring to FIG. 21, t=a and t=b are a start time point and an end time point of one period of angular sections, respectively, and the target time point Ttarget is set to a mid time point in the one period of angular sections. As described above with reference to FIGS. 20A and 20B, if pieces of projection data acquired during an angular section adjacent to the target time point Ttarget are backprojected, only surfaces 2142 through 2145 arranged in a horizontal direction in the partial image 2141 are shown. Surfaces that are not imaged in the partial image 2141 are imaged using pieces of projection data acquired during angular sections in the one period of angular sections, other than the third angular section 2103 including the target time point Ttarget.

When imaging the surfaces that are not imaged in the partial image 2141, the image processing unit 820 may perform motion correction based on the first information in order to minimize blurring.

In detail, surfaces or partial regions shown in the partial image 2121 acquired during the first angular section 2101 are corrected based on the first information 2180. Referring to the first information 2180, the amounts of motion W at the time points a and b are W11 and W12, respectively. For convenience of explanation, it is assumed that the amounts of motion W at time points t11 and t15 respectively included in the first and fifth angular sections 2101 and 2105 are the same as W11 and W12 at the time points a and b, respectively. It is also assumed that the amount of motion of the object at the target time point t13 is C1. In this case, a surface of the object at the time point t13 may be accurately obtained by warping an object in the partial image 2121 corresponding to the first angular section 2101 by the amount of motion (C1-W11). Thus, a corrected partial image 2122 is generated by performing motion correction on the partial image 2121 based on the amount of motion 2124 that has occurred during an interval between time points a and t13 against the total amount of motion (W12-W11) that has occurred during one period of angular sections. In this case, a total amount of motion 2123 is the total amount of motion W12-W11 that has occurred during one period of angular sections, and the amount of motion 2124 may correspond to a difference C1-W11 between the amounts of motion W11 and C1 at the start time point a and the target time point Ttarget t13. In detail, the total amount of motion 2123 may be a value corresponding to a MVF between images at the time points a and b. For example, the total amount of motion 2123 may be a value obtained by converting a sum of absolute values of all motion vectors in the MVF between the images at the time points a and b to a weighted value.

Motion correction is also performed during the remaining angular sections 2102 through 2105 in the same manner as during the first angular section 2101. In detail, a corrected partial image 2132 is generated by performing motion correction on a partial image 2131, which is obtained by backprojecting pieces of projection data acquired during the second angular section 2102, based on the amount of motion 2134 that has occurred during an interval between time point t12 and the target time point Ttarget t13 against the total amount of motion 2123.

Furthermore, a corrected partial image 2162 is generated by performing motion correction on a partial image 2161, which is obtained by backprojecting pieces of projection data acquired during the fifth angular section 2105, based on the amount of motion 2164 that has occurred during an interval between the end time point t=b and the target time point Ttarget t13 against the total amount of motion 2123. Furthermore, a corrected partial image 2152 is generated by performing motion correction on a partial image 2151, which is obtained by backprojecting pieces of projection data acquired during the fourth angular section 2104, based on the amount of motion 2154 that has occurred during an interval between time point t14 and the target time point Ttarget t13 against the total amount of motion 2123.

In this case, motion correction using pieces of projection data acquired before the target time point Ttarget t13 is performed in the opposite direction to motion correction using pieces of projection data acquired after the target time point Ttarget t13. In detail, referring to the first information 2180, motion correction is performed in a direction 2185 that the amount of motion W increases at time points after the target time point Ttarget and in a direction 2186 that the amount of motion W decreases at time points before the target time point Ttarget. Thus, FIG. 21 shows that a direction of the total amount of motion 2123 at the time point t11 is opposite to a direction of the total amount of motion 2123 at the time point t15.

A final tomography image 2170 corresponding to the target time point Ttarget t13 may be reconstructed using the corrected partial images 2122, 2132, 2152, and 2162 and the partial image 2141 acquired during the third time interval 2103 including the target time point Ttarget t13. In this case, since the corrected partial images 2122, 2132, 2152, and 2162 accurately reflects the state of motion of the object at the time point t13, the final tomography image 2170 reconstructed by performing motion correction based on the first information 2180 may have minimized motion artifacts.

According to exemplary embodiments, the image processing unit 820 may generate the final tomography image 2170 by performing motion correction on a tomography image reconstructed from raw data acquired during one period of angular sections based on the first information 2180, and thus, motion artifacts may be reduced.

Furthermore, although FIG. 21 illustrates an example where one period of angular sections is divided into a plurality of angular sections, and motion correction is performed on each of backprojected images corresponding to the plurality of angular sections, motion correction may be performed on a partial image obtained by backprojecting projection data acquired at each of a plurality of views in the one period of angular sections, or be performed during backprojection of projection data acquired at each of a plurality of views. Alternatively, motion correction may be performed on a partial image obtained by backprojecting pieces of projection data acquired for a view group including several views or during backprojection of the pieces of projection data acquired for the view group.

Furthermore, although FIG. 21 shows an example where motion correction is performed on partial images, motion correction may be performed on projection data corresponding to each view, and then FBP may be performed on pieces of corrected projection data to reconstruct a target image.

Figure 22:
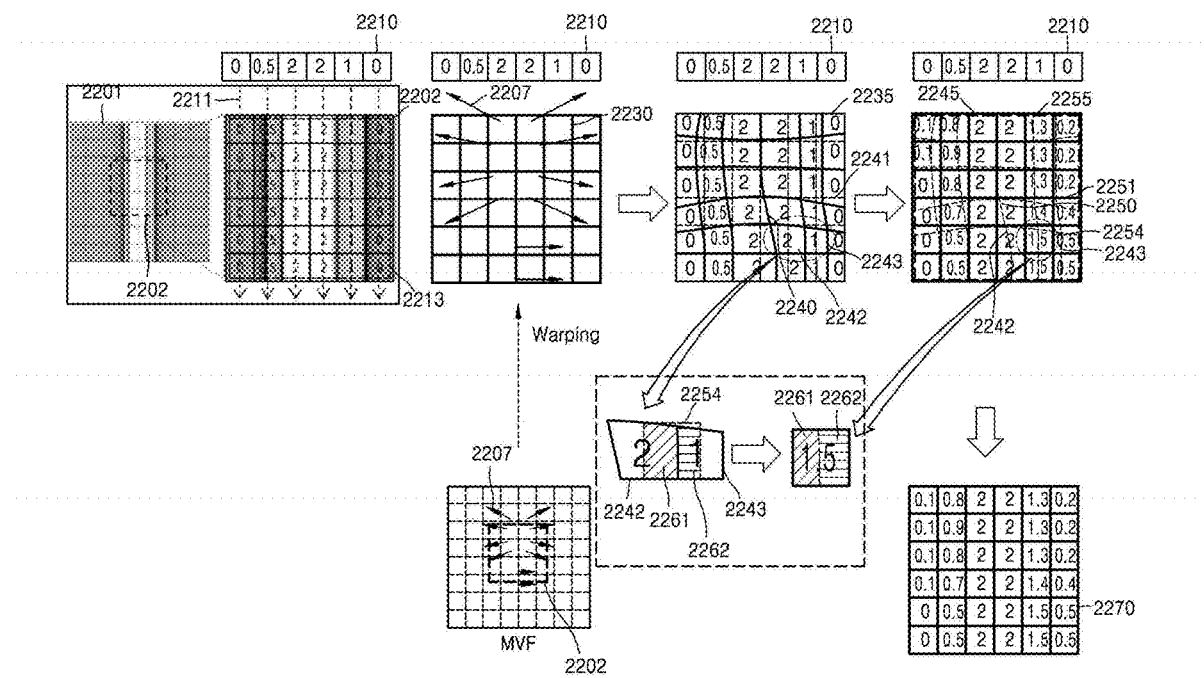
FIG. 22 is a diagram for explaining warping used for reconstructing a tomography image.

FIG. 22 is a diagram for explaining warping used for reconstructing a tomography image.

To reconstruct a target image, the image processing unit 820 performs backprojection whereby pieces of filtered projection data acquired at a plurality of views in one period of angular sections are spread over an image domain 2201 representing an object. Backprojection performed on a region 2202 in the image domain 2201 is now described. The 'region' 2202 may be image data including pixel values as shown in FIG. 22 or an image itself represented by pixel values. Furthermore, the 'region' 2202 may be an image space itself for imaging an object. FIG. 22 illustrates an example where backprojection is performed on filtered projection data 2210 acquired by emitting X-rays in a direction 2211 from first time point T1 that is a start time point of one period of angular sections. In this case, pieces of image data included in the region 2202 may be referred to as backprojected projection data'.

Referring to FIG. 22, the image processing unit 820 may warp an image grid consisting of a plurality of pixels for imaging the object according to the amount of motion of the object at a target time point Ttarget based on first information and reconstruct a target image by using the warped image grid.

In detail, the image processing unit 820 applies the pieces of filtered projection data 2210 to the image grid in the region 2202. In this case, spreading the pieces of filtered projection data 2210 into the image grid that is an image space is referred to as backprojection'.

As the pieces of filtered projection data 2210 are applied to the image grid, the region 2202 is filled with pixel values 2213. If motion of the object does not occur, motion artifacts may not be introduced into a reconstructed target image even when the object is imaged by accumulating the pieces of filtered projection data 2210 corresponding to each view and applying them to the image grid. However, when motion of the object occurs during one period of angular sections, there is a difference between surfaces representing the same portion of the object in the pieces of filtered projection data 2210 acquired at each view. Due to the difference, if the object is imaged by accumulating the pieces of filtered projection data 2210 and spreading them into the image grid, motion artifacts are introduced into a reconstructed target image.

According to an exemplary embodiment, to minimize motion artifacts caused by a moving object, motion correction is performed as described with reference to FIG. 21. Warping of the image grid by the image processing unit 820 for motion correction is now described in detail.

By using first information indicating motion of the object, the image processing unit 820 may warp an image grid 2230 for imaging the same portion as the region 2202 according to a MVF representing the amount of the motion of the object to a target time point in the region 2202. For example, a left upper region of the image grid 2203 may be warped according to a MVF 2207. In this case, the MVF 2207 represents the amount of motion of a surface of the object, i.e., the amount of motion of the object in the first information.

Then, an image grid 2240 that is a warped version of the image grid 2230 is created. The image processing unit 820 spreads pixel values in the pieces of filtered projection data 2210 into the image grid 2240 and accordingly, a region 2235 corresponding to the region 2202 contain the pixel values as shown in FIG. 22. In the region 2235, a quadrangular image grid 2241 indicated by a dashed line represents a common image grid that has not undergone warping.

Furthermore, the image processing unit 820 resamples the region 2235 containing the pixel values in the image grid

2240 to a region 2245 containing pixel values in the quadrangular image grid 2241. In detail, the image processing unit 820 converts the pixel values in the image grid 2240 to pixel values in the Cartesian coordinate system by performing interpolation of the pixel values in the image grid 2240 using a quadratic image pixel matrix.

Resampling of values of pixels 2242 and 2243 in the image grid 2240 to a value of a pixel 2254 in the quadrangular image grid 2251 is now described. The pixel 2242 in the image grid 2240 has a signal value '2', and the pixel 2243 has a signal value '1'. In other words, since a signal value contained in the whole pixel 2242 is 2, the signal value '2' is dispersed according to a ratio of an area within the pixel 2242. Thus, a partial region 2261 corresponding to half the entire area of the pixel 2242 may contain the signal value '1'. Furthermore, since a signal value contained in the whole pixel 2243 is 1, the signal value '1' is dispersed according to a ratio of an area within the pixel 2243. Thus, a partial region 2262 corresponding to half the entire area of the pixel 2243 may contain the signal value '0.5'. Furthermore, the value of the pixel 2254 in the quadrangular image grid 2241 (2251) including the partial regions 2261 and 2262 may contain a signal value '1.5' that is a sum of the signal values '1' and '0.5' of the partial regions 2261 and 2262.

Thus, the resampled region 2245 may include pixel values 2255 arranged in the quadrangular image grid 2251. Thus, the pixel values 2255 in the region 2245 may be generated by resampling all pixels contained in the region 2235.

Furthermore, pixel values arranged in a warped version of image grid may be converted to pixel values arranged in a quadrangular image grid by using various methods other than that described above.

Furthermore, motion correction based on warping may be performed on each of a plurality of pieces of backprojected projection data corresponding to a plurality of views in one period of angular sections. Then, a final tomography image that is a target image may be reconstructed by accumulating a plurality of pieces of backprojected projection data that underwent motion correction.

Furthermore, motion correction based on warping of an image grid may be performed every predetermined angular sections or for each group of views obtained by dividing a plurality of views into several groups, instead of for each view.

In the above-described example, the image processing unit 820 may generate motion corrected image data 2270 by using an warped version of an image grid based on the first information.

Figure 23:
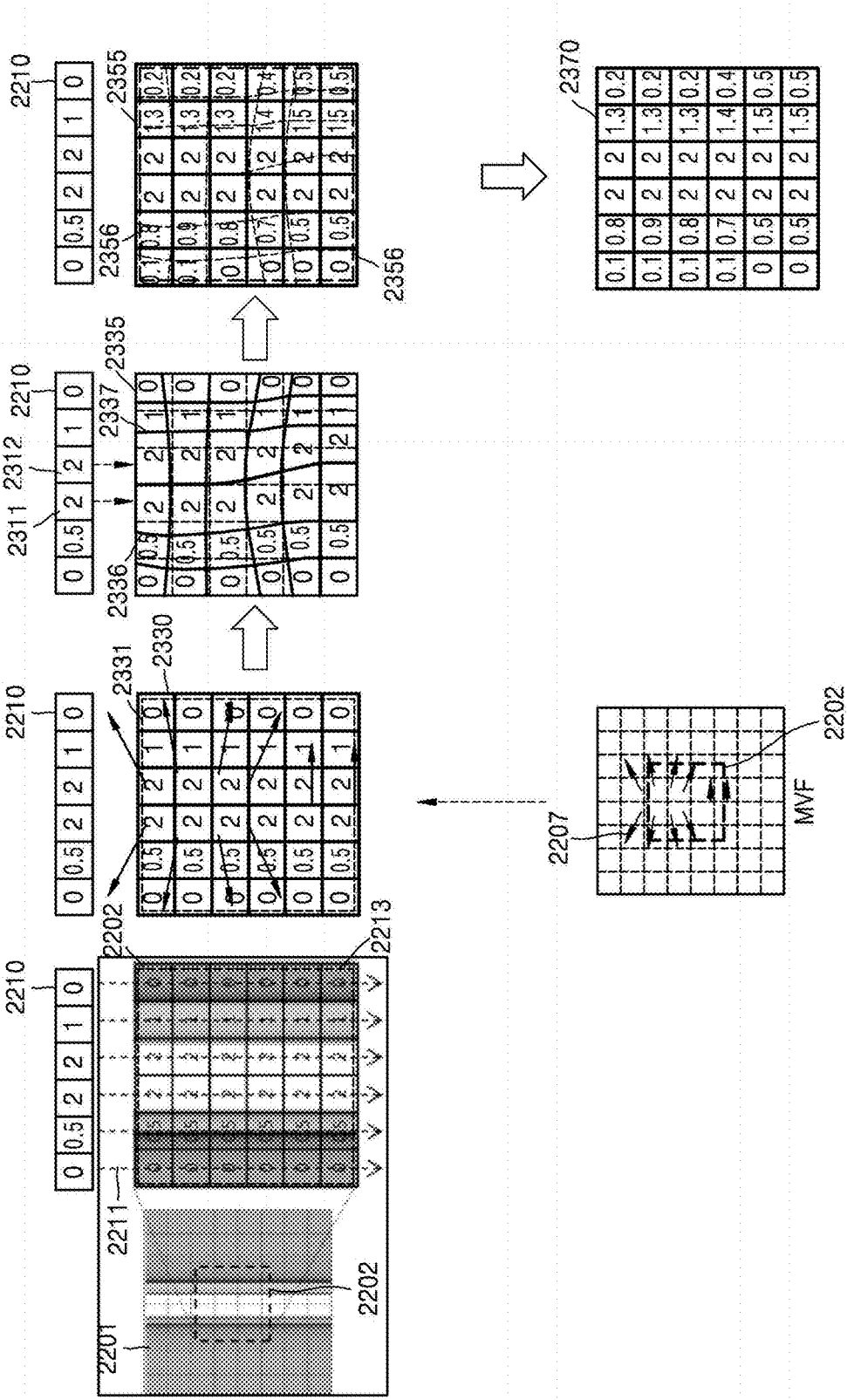
FIG. 23 is another diagram for explaining warping used for reconstructing a tomography image.

FIG. 23 is another diagram for explaining warping used for reconstructing a tomography image. The same descriptions as those provided above with respect to FIG. 22 are omitted.

The image processing unit 820 may generate a motion-corrected final tomography image by warping a backprojected image according to first information. In detail, the image processing unit 820 may reconstruct a final tomography image by warping pixels corresponding to data acquired from a tomography scan based on the first information during backprojection. For reconstruction of the final tomography image, the image processing unit 820 may warp the pixels according to the amount of motion of the object at a target time point Ttarget.

Referring to FIG. 23, pixels in an image (or image data) 2330 generated by backprojecting filtered projection data 2210 may be warped based on a MVF 2207 representing the amount of motion in the first information. Pixel values 2331 in the image 2330 are warped to generate a warped version of an image 2335, and thus, the pixel values 2331 correspond to motion of the object at the target time point Ttarget based on the MVF 2207. In detail, filtered projection data 2311 corresponds to pixel values 2336 in the warped version of image 2335, and the filtered projection data 2312 corresponds to pixel values 2337 in the warped version of image 2335.

Furthermore, the image processing unit 820 may generate a motion corrected image 2355 by performing resampling using the method described with reference to FIG. 22. Pixel values 2356 in the motion corrected image 2355 accurately reflect motion of the object at the target time point Ttarget. Thus, a reconstructed final tomography image may have minimized motion artifacts.

Figure 24:
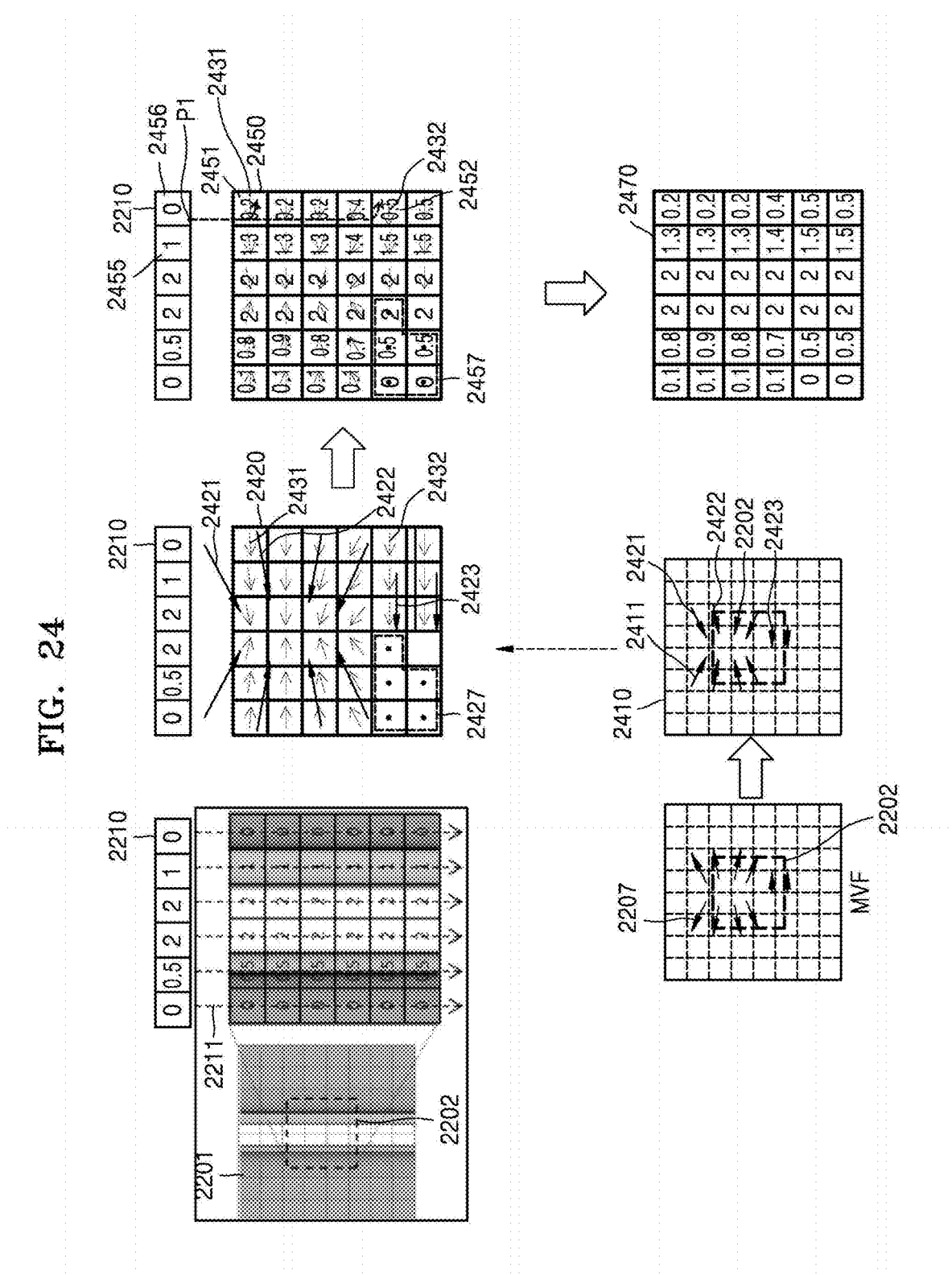
FIG. 24 is another diagram for explaining warping used for reconstructing a tomography image.

FIG. 24 is another diagram for explaining warping used for reconstructing a tomography image.

The same descriptions as those provided above with respect to FIGS. 22 and 23 will be omitted here. The image processing unit 820 may perform motion correction based on first information during backprojection. In detail, the image processing unit 820 may reconstruct a target image by warping a center of a voxel representing an object based on the first information and performing backprojection based on a warped voxel position. In this case, a voxel is a unit space in a virtual 3D grid space for imaging an object. FIG. 24 illustrates an example where a virtual space for imaging the object consists of pixels in a 2D grid space instead of voxels in a 3D grid space.

In detail, if a pixel value at a predetermined position in an image to be reconstructed is affected by motion at each time point, the image processing unit 820 may find a pixel in a detector array from which a value is to be fetched by using an MVF representing the amount of motion from the target time point Ttarget t13 to each time point. For a voxel representing an object at a target time point, in order to backproject onto the voxel filtered projection data corresponding to a view at a time point other than the target time point Ttarget, a destination to which the voxel is to be moved at the time point needs to be computed by reflecting motion of the object Furthermore, the amount of motion of the voxel needed for compensating for the motion of the object may be calculated using an inverse MVF of the MVF representing the amount of motion of the object from the time point to the target time point Ttarget. After the position of the voxel is moved by the calculated amount of compensation, the image processing unit 820 may calculate a pixel in the detector array, from which a value is to be fetched.

In detail, referring to FIG. 24, the image processing unit 820 generates an inverse MVF 2410 by performing field inversion on a MVF representing the amount of motion of the object at the target time point Ttarget and indicated in the first information. Then, a position of each pixel in a backprojected image 2410 is moved using the inverse MVF 2410.

For example, positions of pixels in the backprojected image 2420 are respectively moved based on motion vectors 2411, 2421, 2422, and 2423 in the inverse MVF 2410. In detail, a first rightmost pixel of an uppermost row of the backprojected image 2420 is moved based on the motion vectors 2421 and 2422 (2431). A first rightmost pixel of a fifth row of the backprojected image 2420 is moved based on the motion vector 2423 (2432). Furthermore, a position of a pixel in a region 2427 where no motion is detected based on the inverse MVF 2410 is not moved.

Furthermore, to acquire the backprojected image 2420, the image processing unit 820 calculates a position in the detector array corresponding to a position onto which a pixel value of a predetermined pixel is projected, by taking into account the moved positions of the pixels, fetches filtered projection data 2210 from the position, and accumulates a value corresponding to the filtered projection data 2210 into the predetermined pixel (voxel).

For example, by taking into account a position to which a first rightmost pixel 2451 of an uppermost row of a backprojected image 2450 is moved (2431), a center of the first rightmost pixel 2451 may be acquired using a pixel value at a point P1 in the filtered projection data 2210. Since the point P1 is located not at the center of a first rightmost pixel 2456 of an uppermost row in the filtered projection data 2210 but toward a second rightmost pixel 2455 of the uppermost row, the point P1 is affected by the first and second rightmost pixels 2456 and 2455. Thus, a pixel 2451 has a pixel value '0.2' as shown in FIG. 24 because the first and second rightmost pixels 2456 and 2455 have pixel values '0' and '1', respectively.

Similarly, as a first rightmost pixel 2452 of a fifth row of the backprojected image 2450 moves (2432), the first rightmost pixel 2452 has a center located at surfaces of the first rightmost pixel 2452 and a pixel 2457 as shown in FIG. 24. Thus, the first rightmost pixel 2452 is affected equally by the first and second rightmost pixels 2456 and 2455. Thus, the first rightmost pixel 2452 may have a pixel value '0.5' that is a middle value between the values '0' and '1' of the first and second rightmost pixels 2456 and 2455.

As described above, the image processing unit 820 may obtain a motion corrected target image 2470 that is motion corrected backprojected image obtained by warping a voxel based on an inverse MVF rather than by using warping described with reference to FIGS. 22 and 23.

Figure 25:
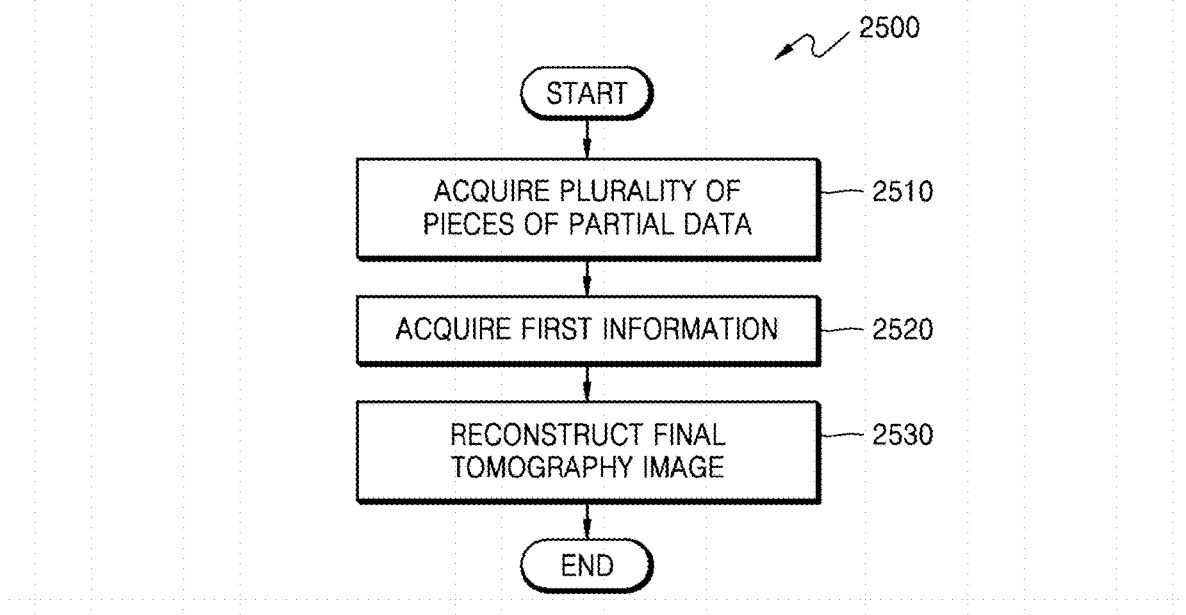
FIG. 25 is a flowchart of a method of reconstructing a tomography image according to an exemplary embodiment.

FIG. 25 is a flowchart of a method 2500 of reconstructing a tomography image according to an exemplary embodiment. Operations included the method 2500 are the same as their corresponding operations performed by the tomography imaging apparatuses 700 and 800 according to the exemplary embodiments described with reference to FIGS. 1 through 24. Thus, the same descriptions that are provided above with respect to FIGS. 1 through 24 are omitted.

According to the method 2500, a plurality of pieces of partial data respectively corresponding to a plurality of consecutive angular sections are acquired by performing a tomography scan on a moving object (operation 2510). In this case, operation 2510 may be performed by the data acquisition unit 810.

Global motion of the object and motion of a first region included in the object are measured based on the plurality of pieces of partial data acquired in operation 2510, and first information representing motion of the object is acquired by reflecting the global motion in the motion of the first region (operation 2520). Operation 2520 may be performed by the image processing unit 820.

In detail, operation 2520 may include comparing two pieces of partial data respectively corresponding to two adjacent angular sections among the plurality of pieces of partial data and acquiring the first information based on a comparison result. Furthermore, the global motion may be measured using rigid registration, and the motion of the first region may be measured using non-rigid registration.

A final image representing the object is reconstructed based on the first information acquired in operation 2520 (operation 2530). Operation 2530 may be performed by the image processing unit 820. In detail, operation 2530 may include reconstructing the final tomography image by correcting motion of the object in a tomography image of the object based on the first information.

As described above, in the tomography imaging apparatuses and the method of reconstructing a tomography image according to one or more exemplary embodiments, global motion of an object and motion of the first region included in the object are measured based on a plurality of pieces of partial data. In other words, both the global motion and local motion of the object are measured using partial data having a high temporal resolution, and thus the motion of the object may be measured with a high degree of accuracy. Furthermore, by performing motion correction based on the measured motion, a final tomography image having significantly reduced motion artifacts may be reconstructed and output.

Thus, the quality of a finally reconstructed tomography image may be improved. The tomography imaging apparatuses and the method of reconstructing a tomography image allow the user, e.g., a medical practitioner to examine an object based on an output final tomography image, thereby allowing easy and accurate diagnosis of a disease of the object.

The embodiments of the inventive concept may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

While one or more embodiments of the inventive concept have been described with reference to the figures, it will be understood by those of ordinary skill in the art that various changes in form and details may be made therein without departing from the spirit and scope of the inventive concept as defined by the following claims. Accordingly, the above embodiments and all aspects thereof are examples only and are not limiting.

What is claimed is:

1. A tomography imaging apparatus comprising:
   a data acquisition unit configured to acquire a plurality of partial data respectively corresponding to a plurality of consecutive angular sections by performing a tomography scan on a moving object; and
   an image processing unit configured to measure global motion of the object and motion of a first region in the object based on the plurality of partial data, acquire first information representing motion of the object by reflecting the global motion in the motion of the first region, and reconstruct a final tomography image representing the object based on the first information.

2. The tomography imaging apparatus of claim 1, wherein the image processing unit reconstructs the final tomography image by correcting the motion of the object in a tomography image representing the object based on the first information.

3. The tomography imaging apparatus of claim 1, wherein the image processing unit compares two partial data respectively corresponding to two adjacent angular sections among the plurality of partial data with each other and acquires the first information based on a comparison result.

4. The tomography imaging apparatus of claim 3, wherein the image processing unit compares two partial images respectively corresponding to the two adjacent angular sections and reconstructed according to a partial angle reconstruction (PAR) method with each other and acquires the first information based on a comparison result.

5. The tomography imaging apparatus of claim 1, wherein each of the plurality of angular sections has a value less than 180°.

6. The tomography imaging apparatus of claim 1, wherein the global motion comprises at least one of translation and rotation of the object, and wherein the motion of the first region comprises motion that occurs due to characteristics of an organ or body part included in the first region.

7. The tomography imaging apparatus of claim 6, wherein the motion of the first region comprises motion of a body part, which occurs in the first region due to at least one of respiration, heartbeat, and generation of a biological signal.

8. The tomography imaging apparatus of claim 1, wherein the image processing unit acquires a plurality of partial tomography images respectively corresponding to the plurality of angular sections based on the plurality of partial data and acquires the first information based on a surface of the object imaged in the plurality of partial tomography images.

9. The tomography imaging apparatus of claim 1, wherein the image processing unit masks at least one body part included in the object in each of the plurality of partial tomography images and measures motion of an edge included in the masked at least one body part as the global motion.

10. The tomography imaging apparatus of claim 9, wherein the image processing unit masks a body part including at least one of ribs and vertebra in each of a plurality of partial tomography images.

11. The tomography imaging apparatus of claim 1, wherein the image processing unit measures the global motion by using rigid registration.

12. The tomography imaging apparatus of claim 1, wherein the image processing unit measures the motion of the first region by using non-rigid registration.

13. The tomography imaging apparatus of claim 1, wherein the image processing unit reconstructs the final tomography image by primarily correcting the global motion of the object in a tomography image representing the object based on the first information and secondarily correcting the motion of the first region in the primarily corrected tomography image.

14. The tomography imaging apparatus of claim 1, further comprising a display unit configured to display the final tomography image.

15. The tomography imaging apparatus of claim 1, further comprising a communication unit configured to transmit the final tomography image to at least one of an external server, medical imaging apparatus, and computing device.

16. The tomography imaging apparatus of claim 1, wherein the image processing unit generates second information comprising information about the motion of the object based on the first information.

17. The tomography imaging apparatus of claim 16, further comprising a display unit configured to display a screen indicating the second information.

18. The tomography imaging apparatus of claim 16, wherein the second information comprises an amount of the motion of the object classified into a plurality of stages.

19. The tomography imaging apparatus of claim 16, wherein the second information comprises the type of the motion of the object.

20. The tomography imaging apparatus of claim 16, wherein the second information comprises the motion of the object classified into a plurality of stages.

21. The tomography imaging apparatus of claim 16, wherein the second information comprises information indicating whether rescanning is required based on an amount of the motion of the object.

22. The tomography imaging apparatus of claim 1, wherein the image processing unit controls an alarm signal notifying rescanning to be output when it is determined that the motion of the object occurs in an amount greater than or equal to a threshold value based on the first information.

23. A method of reconstructing a tomography image, the method comprising:

acquiring a plurality of partial data respectively corresponding to a plurality of consecutive angular sections by performing a tomography scan on a moving object;

measuring global motion of the object and motion of a first region in the object based on the plurality of partial data and acquiring first information representing motion of the object by reflecting the global motion in the motion of the first region; and reconstructing a final tomography image representing the object based on the first information.

24. The method of claim 23, wherein the reconstructing of the final tomography image comprises reconstructing the final tomography image by correcting the motion of the object in a tomography image representing the object based on the first information.

25. The method of claim 23, wherein the acquiring of the first information comprises comparing two partial data respectively corresponding to two adjacent angular sections among the plurality of partial data with each other and acquiring the first information based on a comparison result.

26. The method of claim 23, wherein the global motion comprises at least one of translation and rotation of the object, and wherein the motion of the first region comprises motion that occurs due to characteristics of an organ or body part included in the first region.

27. The method of claim 23, wherein the motion of the first region comprises motion of a body part, which occurs in the first region due to at least one of respiration, heartbeat, and generation of a biological signal.

28. The method of claim 23, wherein, in the acquiring of the first information, the global motion is measured using rigid registration, and the motion of the first region is measured using non-rigid registration.

* * * * *